US011202866B2

(12) United States Patent
Baxter et al.

(10) Patent No.: US 11,202,866 B2
(45) Date of Patent: Dec. 21, 2021

(54) DRUG DELIVERY DEVICE

(71) Applicant: SANOFI, Paris (FR)

(72) Inventors: Elliot Baxter, Warwick (GB); David Aubrey Plumptre, Warwick (GB); Robert Veasey, Warwick (GB); Sophie Louise Sladen, Warwick (GB); Jamie Salter, Warwick (GB)

(73) Assignee: SANOFI, Paris (FR)

( * ) Notice: Subject to any disclaimer, the term of this patent is extended or adjusted under 35 U.S.C. 154(b) by 252 days.

(21) Appl. No.: 16/312,476

(22) PCT Filed: Jun. 30, 2017

(86) PCT No.: PCT/EP2017/066296
§ 371 (c)(1),
(2) Date: Dec. 21, 2018

(87) PCT Pub. No.: WO2018/002314
PCT Pub. Date: Jan. 4, 2018

(65) Prior Publication Data

US 2019/0134313 A1 May 9, 2019

(30) Foreign Application Priority Data

Jul. 1, 2016 (EP) .................................... 16177520
Jan. 25, 2017 (EP) .................................... 17305083

(51) Int. Cl.
*A61M 5/315* (2006.01)
*A61M 5/20* (2006.01)
(Continued)

(52) U.S. Cl.
CPC ............ *A61M 5/3156* (2013.01); *A61M 5/20* (2013.01); *A61M 5/24* (2013.01);
(Continued)

(58) Field of Classification Search
CPC .......... A61M 5/31525; A61M 5/31526; A61M 5/31528; A61M 5/3153; A61M 5/31535;
(Continued)

(56) References Cited

U.S. PATENT DOCUMENTS

2008/0071226 A1 3/2008 Moser et al.
2013/0289518 A1* 10/2013 Butler .............. A61M 5/31561 604/500
2015/0018771 A1 1/2015 Schenker et al.

FOREIGN PATENT DOCUMENTS

CN 103260674 8/2013
CN 103260675 8/2013
(Continued)

OTHER PUBLICATIONS

International Preliminary Report on Patentability in Application No. PCT/EP2017/066296, dated Jan. 1, 2019, 7 pages.
(Continued)

*Primary Examiner* — Emily L Schmidt
*Assistant Examiner* — Leah J Swanson
(74) *Attorney, Agent, or Firm* — Fish & Richardson P.C.

(57) ABSTRACT

A drug delivery device comprises a medicament reservoir attached to a housing, a drive mechanism comprising a plunger movable relative to the housing, a dose selecting element releasably coupled to the drive mechanism and rotatable relative to the housing, a trigger axially movable relative to the housing, and a limiter selectively permitting and preventing axial movement of the trigger depending on the amount of a selected dose. The limiter is constrained to the dose selecting element and to the trigger. One of the limiter or a component part is axially coupled to the housing comprises a track which is in engagement with a blocking feature of the other of the limiter or the component part axially coupled to the housing. The track comprises a narrow section limiting relative movement between the track and
(Continued)

the blocking feature and a wide section permitting relative movement between the track and the blocking feature.

26 Claims, 8 Drawing Sheets

(51) Int. Cl.
*A61M 5/24* (2006.01)
*A61M 5/31* (2006.01)

(52) U.S. Cl.
CPC ..... *A61M 5/31543* (2013.01); *A61M 5/31553* (2013.01); *A61M 5/31583* (2013.01); *A61M 2005/3126* (2013.01); *A61M 2205/581* (2013.01); *A61M 2205/582* (2013.01)

(58) Field of Classification Search
CPC .......... A61M 5/31536; A61M 5/31541; A61M 5/31543; A61M 5/31545; A61M 5/31548; A61M 5/3155; A61M 5/31551; A61M 5/31553; A61M 5/3156; A61M 5/31561; A61M 5/31563; A61M 2005/3154
See application file for complete search history.

(56) References Cited

FOREIGN PATENT DOCUMENTS

| | | |
|---|---|---|
| CN | 103418057 | 12/2013 |
| CN | 104321096 | 1/2015 |
| CN | 104736188 | 6/2015 |
| CN | 104853790 | 8/2015 |
| CN | 105007964 | 10/2015 |
| CN | 105102032 | 11/2015 |
| CN | 105377340 | 3/2016 |
| CN | 105492048 | 4/2016 |
| EP | 0611035 | 8/1994 |
| EP | 1603611 | 12/2005 |
| EP | 2054112 | 5/2009 |
| EP | 2 262 553 | 12/2010 |
| EP | 1885414 | 11/2012 |
| EP | 3006064 | 4/2016 |
| EP | 3181169 | 6/2017 |
| EP | 2968780 | 9/2019 |
| JP | 2013-506466 | 2/2013 |
| JP | 2013-506468 | 2/2013 |
| JP | 2018-537253 | 12/2018 |
| KR | 20150052061 | 5/2015 |
| WO | WO 2004/078239 | 9/2004 |
| WO | WO 2008/019517 | 2/2008 |
| WO | WO 2009/105909 | 9/2009 |
| WO | WO 2010/139643 | 12/2010 |
| WO | WO 2010/149396 | 12/2010 |
| WO | WO 2011/039233 | 4/2011 |
| WO | WO 2011/039236 | 4/2011 |
| WO | WO 2011/039239 | 4/2011 |
| WO | WO 2012/049139 | 4/2012 |
| WO | WO 2012/049141 | 4/2012 |
| WO | WO 2014/033195 | 3/2014 |
| WO | WO 2014/060369 | 4/2014 |
| WO | WO 2014/099831 | 6/2014 |
| WO | WO 2014/128155 | 8/2014 |
| WO | WO 2014/166908 | 10/2014 |
| WO | WO 2015/007819 | 1/2015 |
| WO | WO 2015/032782 | 3/2015 |
| WO | WO 2015/121080 | 8/2015 |
| WO | WO 2015/150578 | 10/2015 |
| WO | WO 2016/001299 | 1/2016 |
| WO | WO 2016/055621 | 4/2016 |
| WO | WO 2016/083384 | 6/2016 |
| WO | WO 2017/102393 | 6/2017 |

OTHER PUBLICATIONS

International Search Report and Written Opinion in Application No. PCT/EP2017/066296, dated Aug. 30, 2017, 10 pages.

Xiping, "The Research Report on Auto-Safety Syringes", China Medical Device Information, Sep. 2008, 14(9):18-25, 9 pages (With Machine Translation).

Smith et al., "A novel, native-format bispecific antibody triggering T-cell killing of B-cells is robustly active in mouse tumor models and cynomolgus monkeys", Scientific Reports, Dec. 2015, 5(17943):1-12.

* cited by examiner

Fig. 21a
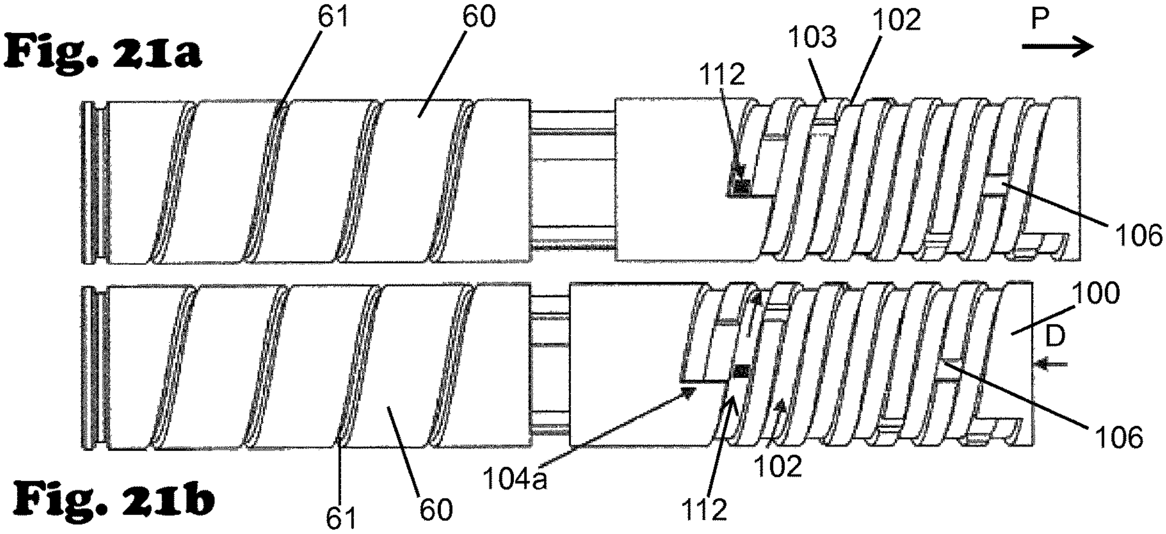
Fig. 21b
Fig. 22
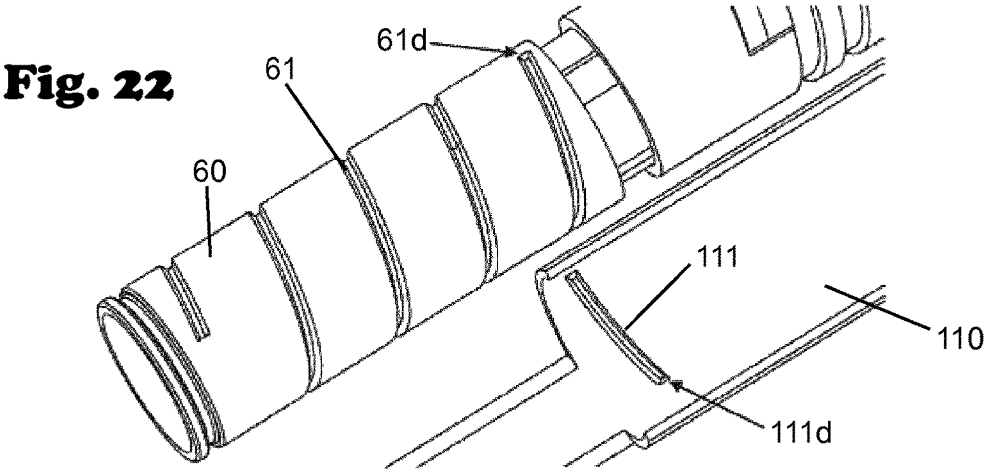
Fig. 23a
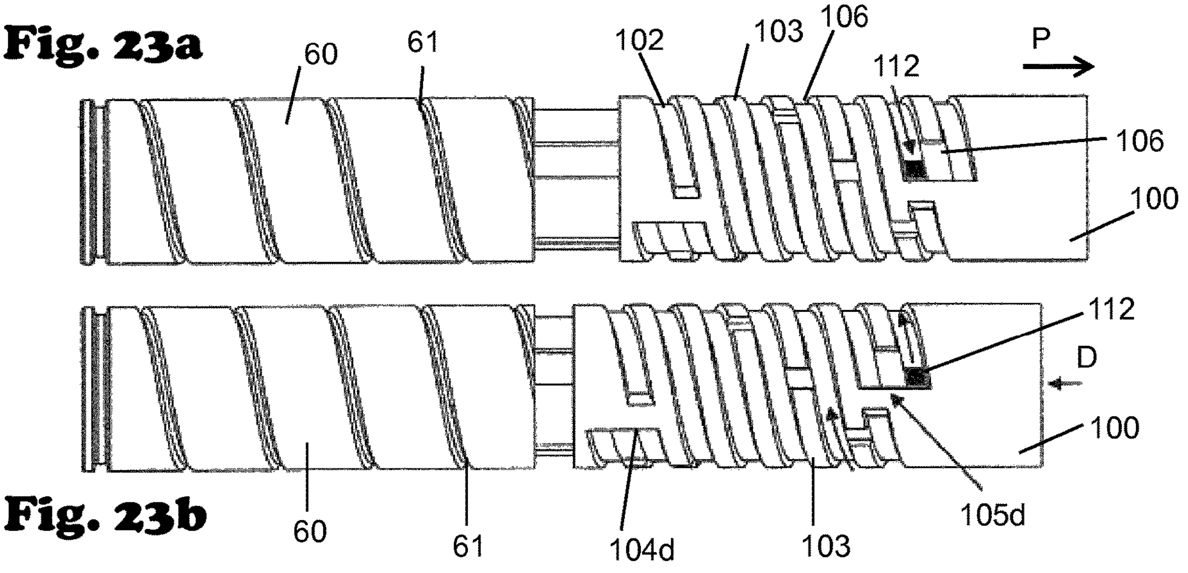
Fig. 23b

Fig. 24a
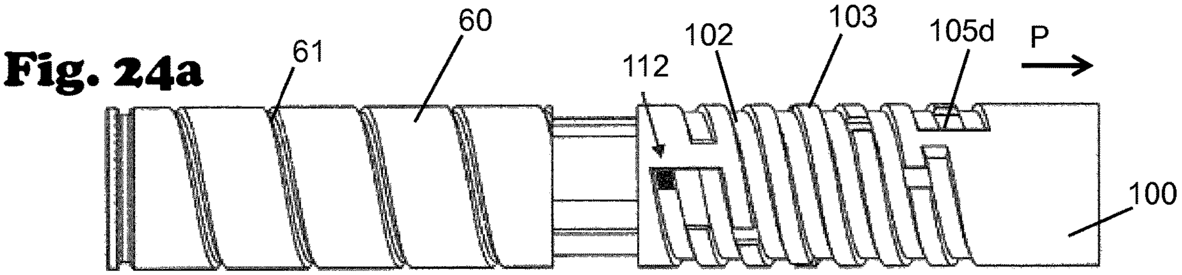
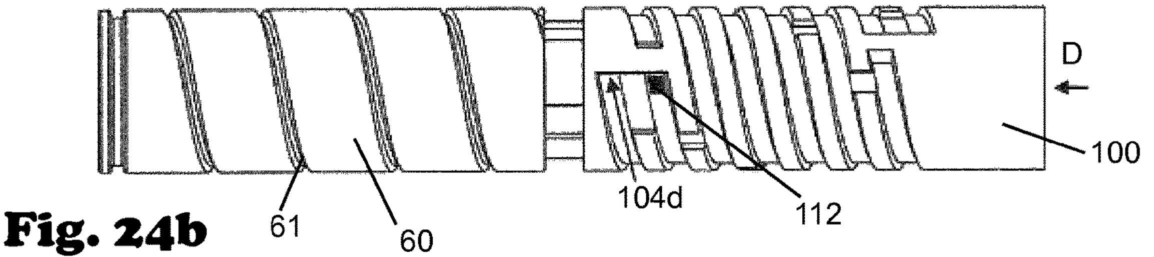
Fig. 24b
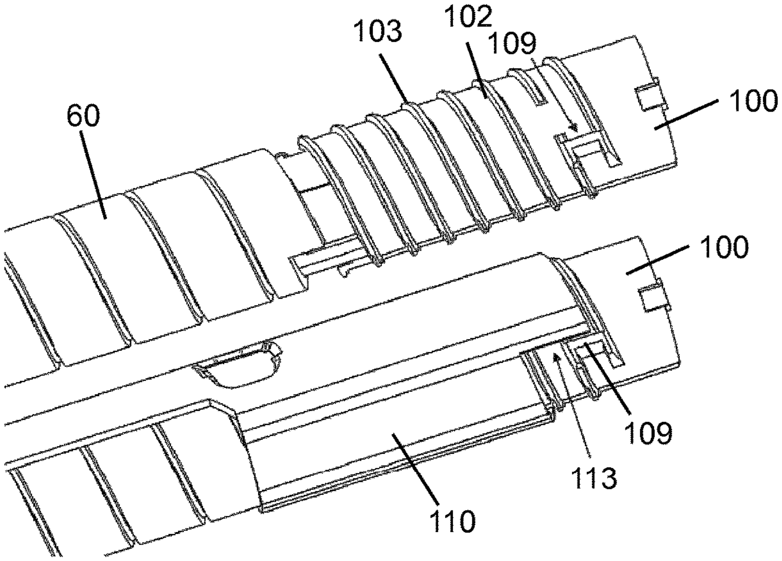
Fig. 25a
Fig. 25b
Fig. 26a
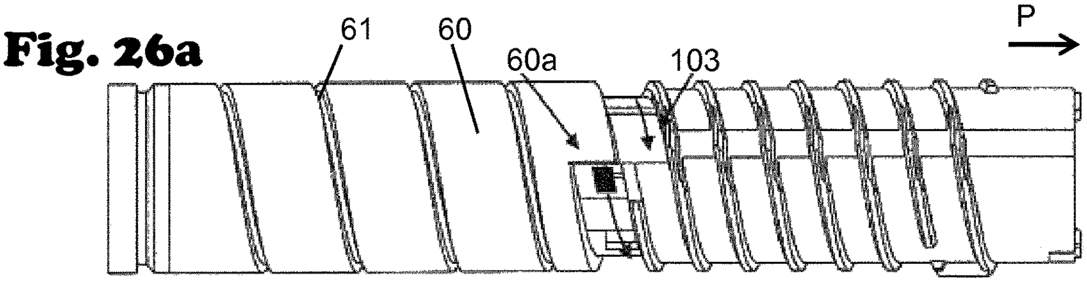
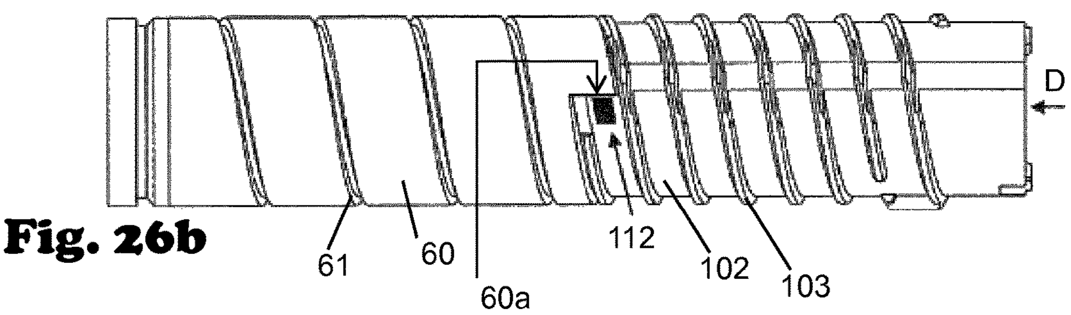
Fig. 26b

DRUG DELIVERY DEVICE

CROSS REFERENCE TO RELATED APPLICATIONS

The present application is a national stage entry of International Patent Application No. PCT/EP2017/066296, filed on Jun. 30, 2017, and claims priority to European Patent Application Nos. 16177520.0, filed on Jul. 1, 2016, and 17305083.2, filed on Jan. 25, 2017, the entire contents of each of which are incorporated herein by reference.

TECHNICAL FIELD

This disclosure is generally directed to a drug delivery device for selecting and dispensing a number of, e.g. user variable, doses of a medicament.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

SUMMARY

According to a first aspect, a drug delivery device comprises a medicament reservoir attached to a housing, a drive mechanism, a dose selecting element, a trigger and a limiter. The housing may be an outer housing defining a longitudinal axis of the device extending between a distal end and a proximal end. The housing may be a single component part, e.g. an outer shell of the device, or may comprise several component parts, e.g. an additional inner housing and/or an insert. The drive mechanism may comprise a plunger or piston rod which is axially movable in the distal direction relative to the housing for dispensing one or more doses of a medicament from the medicament reservoir. The drive mechanism may comprise additional component parts, for example a driver engaging the plunger at least during dose dispensing. The dose selecting element may be releasably coupled to the drive mechanism and may be rotatable relative to the housing in a first direction for selecting a dose. The dose selecting element may be a component part which is directly manipulated by a user for dose selecting, e.g. a dial grip, or may be a component part which is rotated relative to the housing for selecting a dose in response to a user manipulating a further component part which is coupled to the dose selecting element at least during dose selecting. The trigger may be axially movable relative to the housing for initiating dispensing of a dose selected by the dose selecting element, i.e. the trigger may be a button which is pressed in the distal direction. Actuation of the trigger may release a clutch and a blocking mechanism within the device thereby permitting that a dispensing force or torque is transmitted from a spring to the drive mechanism. In addition, or as an alternative, actuation of the trigger may cause dose dispensing, e.g. by actuating the drive mechanism by means of the trigger, for example in a manually operated device. Preferably, the limiter selectively permits and prevents axial movement of the trigger depending on the amount of the selected dose. In other words, the limiter may block actuation of the trigger, thereby preventing dose dispensing, if the amount of the selected dose does not correspond to a predefined threshold. The limiter may be rotationally constrained, preferably permanently rotationally constrained, to the dose selecting element and may be axially constrained, preferably permanently axially constrained, to the trigger. Preferably, the limiter comprises a path or track, e.g. a slide way, which is in engagement with a blocking feature, e.g. a slide block, axially coupled to the housing. As an alternative, the track may be provided axially coupled to the housing and the blocking element which engages the track may be axially constrained to the trigger. The track or the blocking feature may be provided on a component part axially coupled to the housing. This includes that the track or the blocking feature is provided directly on the housing. The track may comprise at least one narrow section limiting relative axial movement between the track and the blocking feature, for example substantially preventing relative movement, and at least one wide section permitting relative axial movement between the track and the blocking feature.

The slide way or track of the limiter mechanism and/or the slide block or blocking feature of the limiter mechanism may be provided separately, e.g. axially spaced, from further thread forms, e.g. provided for guiding the dose selecting element. Alternatively, the slide way or track of the limiter mechanism and/or the slide block or blocking feature of the limiter mechanism may be provided at least partially identical with a further thread form, e.g. provided for guiding the dose selecting element, i.e. the slide way of the limiter may be the female thread form of the further thread and/or the slide block may be the male thread form of the further thread (or a still further thread). As a further alternative, the slide way or track of the limiter mechanism and/or the slide block or blocking feature of the limiter mechanism may be provided adjacent to further thread forms, e.g. provided for guiding the dose selecting element. For example, the slide way or track of the limiter mechanism and/or the slide block or blocking feature of the limiter mechanism may be provided overlapping with such further thread forms, e.g. the slide way is a groove located in the space between turns of a female groove form of such a further thread. In the latter case with the limiter mechanism being adjacent to a further thread of the device, the female groove form of this further thread may form or may be part of the at least one wide section permitting relative axial movement between the track (slide way) and the blocking feature (slide block). In other words, if the blocking feature or slide block engages a narrow section defined by the slide way or track, relative axial movement between the track and the blocking feature is limited, whereas the blocking feature or slide block may pass through the wide section of the slide way or track into adjacent female thread form of the further thread, thereby permitting relative axial movement between the track and the blocking feature. The blocking feature or slide block may then be guided in the female thread form of the further thread during dose dispensing.

According to an aspect, the track of a limiter and a corresponding blocking element are designed and arranged such that actuation of the trigger, that is to say initiating dose dispensing, is prevented by restricting or preventing axial movement of the limiter and of the trigger which is coupled to the limiter as long as the blocking element engages the narrow section of the track. On the other hand, axial movement of the limiter and of the trigger which is coupled to the limiter is allowed as long as the blocking element engages the wide section of the track by permitting relative axial movement of the blocking element within the track. Thus, the positions of the narrow and wide sections of the track define amounts of the selected dose in which dose dispensing is prevented (narrow section) or permitted (wide section). The length of the narrow and wide sections can be varied as desired to increase or limit the range of selected dose values for which dispensing is permitted.

For example, dose dispensing may be permitted for a priming operation to be undertaken before each dose is administered by providing a wide section of the track at a position corresponding to a range of zero to just a few units, e.g. 2 or 3 units. Further, a wide section may be provided at a position corresponding to a certain dose value, thus allowing dispensing a dose of this value but preventing dispensing of a smaller or larger dose (except e.g. for a priming dose). Further, a wide section may be provided extending up to a position corresponding to a maximum dose threshold and/or may be provided extending from a position corresponding to a minimum dose threshold.

The drug delivery device with such a limiter can be configured to have a minimum dose value below which the user is unable to dispense medication, e.g. allowing either multiple doses or a single dose to be delivered from the medicament reservoir, such as a glass ampoule. The device may be configured to allow a discrete range of different dose values to be selected by the user, but may also be configured to offer only one dose value that may be dispensed. The device may further allow for priming of the device, with the user being able to dial and deliver a small volume of medication (typically 2 International Units) to check whether flow occurs correctly through the needle. The device may be designed with features that limit the maximum deliverable dose value, which in one embodiment can be configured on the component that also defines the permitted deliverable dose values. This means that both the minimum and maximum deliverable dose values can be set or altered by changing a single component of the device, making it a highly flexible 'platform' for a variety of applications. As mentioned above, the design can be configured with the minimum and maximum selectable dose values arranged so that only a single dose value may be dispensed (i.e. it is a 'fixed' dose device). Alternatively, it can be configured so that only particular sequential, or non-sequential dose values can be dispensed (for example this could be a sequential range of doses such as 10 IU, 11 IU, 12 IU, or a non-sequential range of doses such as 10 IU, 13 IU, 23 IU, etc.).

The track may extend helically about an outer surface of the, e.g. tubular, limiter. This allows selecting doses by rotating the dose selecting element for more than 360°, which typically occurs for selecting relatively large doses of more than 20 IU or 24 IU. As an alternative, the track may extend circumferentially about an outer surface of the, e.g. tubular, limiter, i.e. without a pitch or screw lead. This latter embodiment provides for a very compact design of the limiter which is limited to devices in which dose selecting requires rotating the dose selecting element only up to 360°. As mentioned above, as a further alternative, the track may be provided on the housing or a component part coupled to the housing.

Preferably, the narrow section of the track defines a guidance for the blocking feature which is, at least substantially, free of backlash or play. The wide section of the track may define a guidance for the blocking feature permitting relative axial movement between the track and the blocking feature.

The track may be a groove bounded or defined by at least one intermittent rib. The narrow section of the track may be defined by a portion of the groove in which the rib is present, preferably on the distal and proximal side, while the wide section of the track may be defined by a portion of the groove in which the rib is omitted, preferably by providing a clearance in the rib on the proximal side of the groove. If the track has a helical configuration, it may be permitted that the blocking feature is displaced from one thread form to the next thread form in the wide section, i.e. where the rib is omitted. On the other hand, as long as the blocking feature is in the narrow section with the rib being present, the blocking feature is guided within the thread form, thereby preventing relative axial movement.

Some applications of the device may require that dose dispensing can be interrupted or paused part way through delivery of a dose. This typically requires moving the trigger back to its initial dose selecting position. If the blocking feature is in the narrow section, axial movement of the trigger is prevented, thus preventing interruption of dose dispensing. Preferably, the track and the blocking feature are designed such that the blocking feature is prevented from passing over the narrow section of the track in the axial direction of movement of the trigger, e.g. in the distal direction, for initiating dispensing of a dose, whereas the blocking feature is permitted to pass over the narrow section of the track in a non-destructive manner in the opposite axial direction, e.g. in the proximal direction. Thus, interruption of the dispensing process is possible even if the blocking feature is in the narrow section of the track.

If the user releases the button at a dose value where the blocking feature is aligned with a wide section of the track, then the button is allowed to fully retract—thus permitting re-engagement of the splines between drive sleeve and housing, which also means that the dispense operation is stopped, but can be re-started by pushing the button again. However, if the blocking feature has jumped over the rib of the limiter as described above, dispensing of the dose could not be re-initiated. According to a further embodiment the limiter mechanism is designed so that if the button is released part way through a dose, the blocking feature is pressed, e.g. by a clutch spring, against the rib of the limiter, thus acting as a kind of friction brake. The features are designed so that the friction should be high enough to stop dispensing. That is to say in a spring driven device the torsion spring is not powerful enough to overcome this friction. This design means that the user can then re-start dispensing (by pushing the button again) to continue delivery of the dose.

Upon pausing delivery, the user may be unable to adjust the dose from the preselected value. In order to provide the possibility to pause delivery of a dose and then to continue delivery just by moving the trigger in the axial direction, in another embodiment a face of the at least one intermittent rib of the track directed opposite to the axial movement of the trigger for initiation dispensing of a dose is shallower than a face of the rib pointing in the direction of the axial movement and a face of the blocking feature pointing in the direction of the axial movement is shallower than a face of the blocking feature directed opposite to the axial movement. The face of the at least one intermittent rib of the track directed opposite to the axial movement and the face of the blocking feature pointing in the direction of the axial movement are preferably between 10° and 60° shallower than the respective opposite face of the same component. For example, if the limiter moves in distal direction during dose dispense the proximal face of the at least one intermittent rib of the track is shallower than its distal face and the distal face of the blocking feature is shallower than its proximal face. Accordingly, the at least one intermittent rib of the track and the blocking feature comprise an inclined saw-tooth cross-section, wherein the two shallow faces of the intermittent rib and the blocking feature abut against each other. This embodiment alters the flank angle of the abutting faces in order to increase the friction force at the interface between the two surfaces when they are brought into contact during pausing delivery. This friction force acts to halt dispense.

In another embodiment a face of the at least one intermittent rib directed opposite to the axial movement of the trigger during dose dispense comprises at least one detent sized such that the blocking feature runs in clearance of the detent. Preferably, there is a plurality of such detents at the intermittent rib, more preferably at regular intervals to aid in retarding the relative motion of the track and the blocking feature. For example, if the user ceases to apply a distal force to the trigger during dispense, the limiter is forced proximally into the blocking feature, causing it to come into contact with one of the detents. This contact will act to stop dispense.

In another embodiment the wide section of the track comprises a commit ramp creating a one-way commit feature which allows relative axial movement between the track and the blocking feature during dose dispense when the trigger is activated and blocks the relative movement into the opposite axial direction when the trigger is released in order to stall dose dispense. Accordingly, the commit ramp acts in the axial direction and comprises a shallower inclination at the axial face which is overrun during relative axial movement of track and blocking feature for initiating dispensing of a dose than on the other axial face. The other, opposite axial face blocks relative axial movement between the track and the blocking feature, preventing the limiter from returning past the blocking feature in the proximal direction if the trigger is released at a point where these two features are rotationally aligned.

The dose selecting element may be a tubular number sleeve, e.g. with markings on its outer surface, which is at least partially visible through an aperture or window of the housing. The number sleeve may be in threaded engagement with the housing, for example like the dose dial sleeve coupled to the outer housing as disclosed in EP 1 603 611 B1 or coupled to the inner housing as disclosed in WO 2014/033195 A1, or with a component part coupled to the housing, for example like the gauge element disclosed in WO 2016/001299 A1. Preferably, the limiter is in splined engagement with the dose selecting element such that the limiter is axially movable but not rotatable with respect to the dose selecting element.

The drug delivery device may further comprise a gauge element which is rotationally constrained to the housing and axially movable relative to the housing. The dose selecting element may be coupled to the gauge element by means of a thread. The gauge element may comprise the blocking feature or alternatively the thread guiding the blocking feature of the limiter.

The same effect as indicated above to enable pausing by releasing the trigger and continuing delivery just by moving the trigger in the axial direction again may be applied to the dose selecting element and the gauge element. Accordingly, a proximal face of a rib forming the thread of the gauge element is shallower than a distal face and a proximal face of the groove forming the thread of the dose selecting element is shallower than an opposite distal face. Naturally, a similar effect can be achieved if the thread of the gauge element was a groove and the thread of the dose selecting element was a rib.

In order to provide a limit for the maximum dose a user can dial the gauge element comprises an axial leading edge and an axial trailing edge at its proximal end wherein the leading edge engages with a corresponding stop on the limiter when the maximum dose is reached during dialing. The leading edge of the gauge element may be designed to be axially longer than the trailing edge to ensure that the leading edge engages with the stop on the limiter during dose dialing, while the trailing edge misses the stop feature during dose dispense.

The subject matter described is suitable for manually driven devices and for spring driven devices. Preferably, the dose selecting element is coupled to a power reservoir, like a spring, which is coupled to the housing such that rotation of the dose selecting element during dose selecting accumulates energy in the power reservoir. The energy accumulated in the power reservoir may drive the drive mechanism during dose dispensing.

The drug delivery device may further comprise a clutch operable by the trigger and located between the dose selecting element and the drive mechanism. Preferably, wherein the clutch rotationally couples the dose selecting element and the drive mechanism upon actuation of the trigger and permits relative rotation of, i.e. de-couples, the dose selecting element and the drive mechanism during dose selecting, for example as disclosed in WO 2016/001299 A1. As an alternative, the trigger may actuate a clutch coupling the dose selecting element and the drive mechanism during dose selecting and de-coupling the dose selecting element and the drive mechanism during dose dispensing, for example as disclosed in EP 1 603 611 B1.

Drug delivery devices may have various different drive mechanisms. Examples are disclosed in EP 1 603 611 B1, WO 2014/033195 A1, WO 2016/001299 A1, EP 2 054 112 B1, WO 2010/149396 A1 and EP 2 262 553 B1. Preferably, the drive mechanism further comprises a drive sleeve, wherein the plunger or piston rod is coupled to the housing, for example by means of splines or a thread, and to the drive sleeve, for example by means of splines or a thread, such that rotation of the drive sleeve causes axial movement of the plunger relative to the housing for dispensing doses of the medicament from the medicament reservoir. As an example, the plunger may be in threaded engagement with the housing and in splined or in threaded engagement with the drive sleeve.

Drug delivery devices of the type which allow the user to select the dose value typically comprise a limiter mechanism defining a zero dose stop, i.e. a minimum dose position, and a maximum dose stop, i.e. a position limiting the amount or degree the dose selecting element may be rotated. Such a limiter may comprise one or more separate component parts or may be, at least partially, integrated in the dose selecting element, the housing and/or the drive mechanism. According to a preferred embodiment the track comprises at least one rotational hard stop limiting rotation of the blocking feature relative to the limiter. Thus, the rotational hard stop may be located at a position of the limiter defining the minimum or maximum selectable dose. This feature is independent of the above mentioned limiter mechanism for preventing and/or permitting dispensing of certain selected doses. Preferably, the thread comprises at least one rotational hard stop limiting rotation of the dose selecting element relative to the gauge element, wherein the rotational hard stop is located at a position defining the minimum or maximum selectable dose.

According to an aspect, the limiter mechanism is suitable for use in a drug delivery device having a dose selecting element, e.g. a number sleeve or a component part coupled to a number sleeve, which may be rotated for more than 360° during dose setting. According to a first aspect, in such a device, the dose selecting element may be axially constrained to an inner or outer housing of the device, i.e. the dose selecting element is not axially movable during dose setting, with the dose selecting element being in threaded engagement with a pusher, e.g. a masking pusher like a gauge element, which in turn is in engagement with a limiter having a helical track, preferably with identical pitch as the threaded engagement. The limiter is preferably rotationally constrained to the dose selecting element and axially movable relative to the dose selecting element. In addition, the pusher may engage the helical track of the limiter such that the axial movement of the limiter is delimited by the path defined by the helical track, which comprises sections permitting axial movement of the limiter, e.g. wider sections of the path, and sections preventing axial movement of the limiter, e.g. narrower section of the path. The limiter may be coupled to a button or trigger, thereby limiting axial movement of this button or trigger.

According to a second aspect, in a device with a dose selecting element which may be rotated for more than 360° during dose setting, the dose selecting element may be in threaded engagement with an inner or outer housing such that rotation of the dose selecting element causes axial displacement of the dose selecting element relative to the housing. The dose selecting element may comprise the helical track, preferably with identical pitch as the threaded engagement, i.e. the dose selecting element comprises a limiter path. An axially movable pusher may engage the path which comprises sections permitting axial movement of the pusher, e.g. wider sections of the path, and sections preventing axial movement of the pusher, e.g. narrower section of the path. The pusher may be coupled to a button or trigger, thereby limiting axial movement of this button or trigger.

As a third aspect, the limiter mechanism is suitable for use in a drug delivery device having a dose selecting element, e.g. a number sleeve or a component part coupled to a number sleeve, which may only be rotated for up to 360° during dose setting. Although the limiter track may be helical in such devices, too, it is possible to have a limiter track extending only circumferentially, i.e. without a pitch. A pusher engaging the limiter track and being coupled to a button or trigger may limit axial movement of this button or trigger.

Variations of these three aspects may be provided regarding interaction of the track and the pusher engaging the track. For example, the track and the pusher may be designed that once the pusher has entered a wider section of the track and dose dispensing has been initiated by axial displacement of the button or trigger (with the pusher), dose dispensing may not be stopped or paused because, during dose dispensing, the pusher is guided in a section of the track preventing returning of the button or trigger to the previous axial position, i.e. the dose setting position when the pusher is guided in the narrower section of the track. As an alternative, the track and/or the pusher may be provided with an inclined surface, like a ramp, permitting the pusher to return from a wider section of the track into a smaller section of the track, i.e. axial displacement of the button or trigger in a dose setting position is permitted. As a still further alternative, friction between the pusher and the track may be chosen such that dose dispensing is paused as soon as the button or trigger is released. Friction between the pusher and the track may be tuned e.g. by providing a coating or by providing a rougher or smoother surface, for example, a toothing.

During dose dialing and dispense the positions of the blocking feature and the track, in particular its wide section permitting relative axial movement between the track and the blocking feature are dictated by a chain of other components, each with their own associated manufacturing tolerances. A cumulative effect of these component tolerances could foreseeably result in the limiter, other component and dose selecting element being rotationally misaligned (from their nominal positions) to the point where the blocking feature is still in a narrow section of the track despite the device having been dialed to a permissible dose. Accordingly, the blocking feature and/or the at least one wide section of the track comprises an alignment feature. For example, the wide section of the track may comprise a positive detent and the blocking feature may comprise a corresponding alignment rib at its surface. The positive detent and the alignment rib may run in the axial direction. The wide section of the track and the blocking feature may comprise other suitable structure at its surface as well. In case of a rotational misalignment the interaction of the corresponding ramps (sloped sides) of the rib and ramps (sloped sides) of the positive detent act to guide the two components back towards their nominal position. Further, the blocking feature may comprise lead-in ramps formed on the sides of the blocking feature facing into circumferential direction forming for example tapered edges. At the extremes of tolerance, the lead-in ramp overlaps with the end of the narrow section of the track when a permissible dose is dialed. During dose dispense the blocking feature lead-in ramp leads the blocking feature into the wide section of the track.

In another embodiment the proximal end of a portion comprising the outer thread of the number sleeve comprises an axial edge which forms a minimum dose dial stop for the blocking feature, typically corresponding to the 0 IU dial position.

BRIEF DESCRIPTION OF THE DRAWINGS

Non-limiting, exemplary embodiments will now be described with reference to the accompanying schematic drawings, in which:

FIGS. 21*a* & 21*b* show an enlarged detail of a side view of two components of a drug delivery device according to a ninth embodiment a) in a position in which the maximum dose is dialed and b) in a dispense position;

FIG. 22 shows an enlarged detail of a side view of three components of the drug delivery device according to the ninth embodiment;

FIGS. 23*a* & 23*b* show an enlarged detail of a side view of two components of a drug delivery device according to a tenth embodiment a) in a position in which the maximum dose is dialed and b) in a dispense position;

FIGS. 24*a* & 24*b* show an enlarged detail of a side view of two components of the drug delivery device according the tenth embodiment a) in a position in which the minimum dose is dialed and b) in a dispense position;

FIGS. 25*a* & 25*b* show an enlarged detail of a side view of a drug delivery device according to an eleventh embodiment a) of two components and b) of three components in a position in which the maximum dose is dialed; and FIGS. 26*a* & 26*b* show an enlarged detail of a side view of two components of the drug delivery device according to the eleventh embodiment a) in a position in which a minimum dose is dialed and b) in a dispense position.

DETAILED DESCRIPTION

Figure 1:
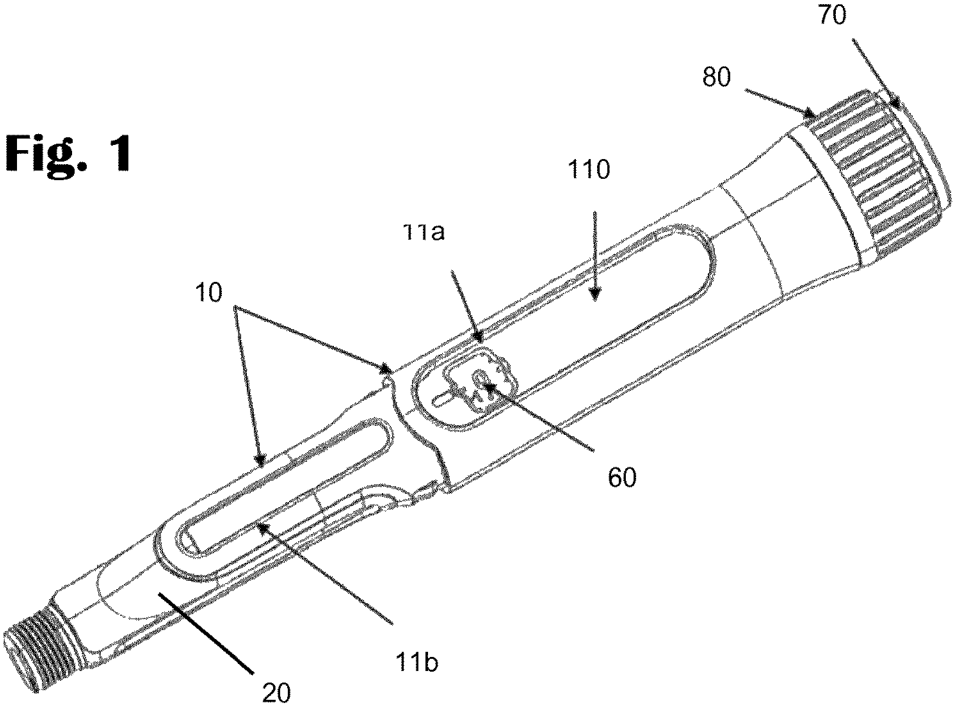
FIG. 1 shows a perspective view of a drug delivery device according to a first embodiment.

The subject matter described is suitable for disposable devices and for reusable devices which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting.

Some stored-energy devices use a combination of spring preload and additional energy provided by the user, for example during dose setting. Manually driven drug delivery devices are known from EP 2 054 112 B1 and WO 2010/149396 A1. A spring driven drug delivery device is known from EP 2 262 553 B1.

WO 2016/001299 A1 discloses an injection device comprising a housing, a spring adapted to provide a force necessary for ejecting a dose from the injection device, and a dose setting member operatively connected to a dose indicator which is positioned within the housing. The dose setting member and the dose indicator cooperate to set the dose to be ejected from the injection device. The dose indicator, during dose setting, is adapted to undergo a rotational movement within the housing and relative to the housing. Further, a gauge element is provided which is rotationally constrained to the housing and axially displaceable relative to the housing. The gauge element and the dose indicator form a limiter mechanism defining a maximum settable dose and/or a minimum settable dose.

Further, EP 1 603 611 B1 and WO 2014/033195 A1 each disclose a manually driven drug delivery device for selecting and dispensing a number of doses of a medicament, the device comprising a medicament reservoir in the form of a cartridge attached to a housing, a drive mechanism comprising a threaded piston rod which is axially movable relative to the housing for dispensing doses of the medicament from the cartridge, a dose selecting element in the form of a threaded number sleeve which is releasably coupled to the drive mechanism and rotatable relative to the housing in a first direction for selecting a dose, and a trigger which is axially movable relative to the housing for initiating dispensing of a dose selected by the dose selecting element.

There are therapies requiring that the minimum dose dispensed and/or the maximum dose dispensed is limited. This may, for example ensure that only a therapeutically effective dose can be administered or it may prevent overdosing. In other applications it may be advantageous to offer a device which allows delivery of only one fixed dose value but also permits a priming operation to be undertaken before each dose is administered.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are, for example, hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is, for example, a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 13 sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are, for example, acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are, for example, hydrates.

A drug delivery device that provides a simple and effective feature that limits deliverable dose values for a variety of different drug delivery devices is described.

FIG. 1 shows a drug delivery device in the form of an injection pen which has a basic design as disclosed in WO 2016/001299 A1. The device has a distal end (left end in FIG. 1) and a proximal end (right end in FIG. 1). The drug delivery device comprises a body or housing 10, a cartridge holder 20, a threaded plunger (piston rod) 30, a drive sleeve 40, a nut 50, a dose indicator (number sleeve) 60, a button 70, a dial grip or dose selector 80, a torsion spring 90, a cartridge (not shown), a limiter 100, a gauge element 110, a clutch plate 120 and a clutch spring 130. A needle arrangement (not shown) with a needle hub and a needle cover may be provided as additional components, which can be exchanged as explained above. All components are located concentrically or essentially concentrically about a common principal axis I (FIG. 2) of the mechanism.

Figure 2:
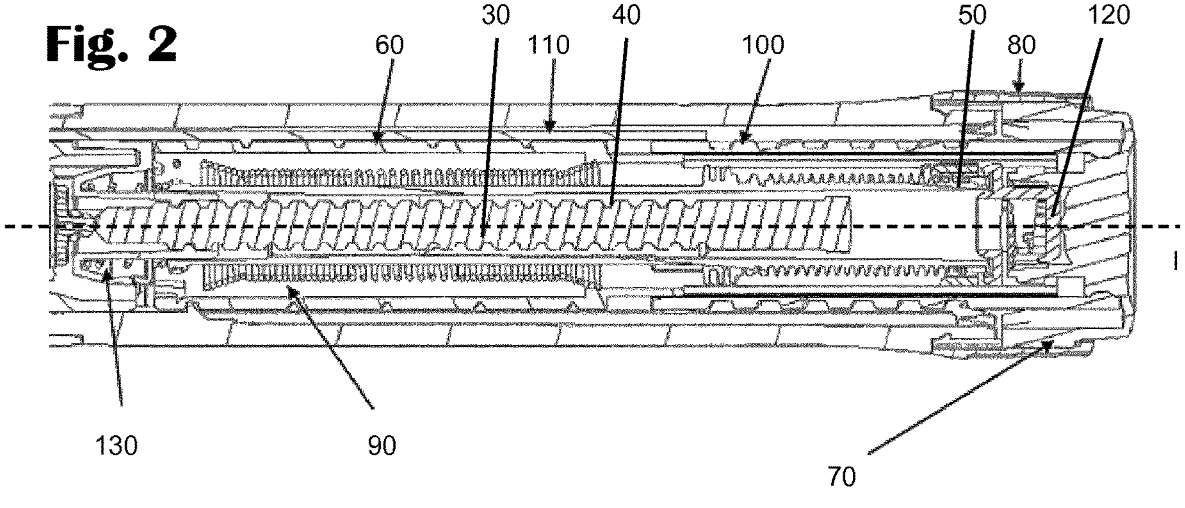
FIG. 2 shows a sectional view of the proximal end of the device of FIG. 1 in a dose setting state.

The housing 10 or body is a generally tubular casing element having a proximal end with an enlarged diameter. The housing 10 provides location for the liquid medication cartridge and cartridge holder 20. As shown in FIGS. 1 and 2, the housing comprises a first dose window 11*a* and a second gauge window (or lens) 11*b* which are incorporated into the housing body e.g. by twin-shot molding. The windows 11*a*, 11*b* may be molded during a first shot in a translucent (and preferably transparent) material, and the outer cover of the housing is molded during a second shot in an opaque material.

The cartridge holder 20 is located at the distal side of housing 10 and permanently attached thereto. The cartridge holder may be a transparent or translucent component which is tubular to receive cartridge. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through a threaded interface with the housing 10. The piston rod 30 is an elongate member with an outer thread engaging the corresponding thread of the housing 10. The interface with the driver 40 comprises at least one longitudinal groove or track of the piston rod 30 and a corresponding protrusion or spline of the driver 40. At its distal end, the piston rod 30 is provided with an interface for clip attachment of a bearing.

The drive sleeve 40 is a hollow member surrounding the piston rod 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

A splined tooth interface with the housing prevents rotation of the drive sleeve 40 during dose setting. This interface comprises a ring of radially extending outer teeth at the distal end of drive sleeve 40 and corresponding radially extending inner teeth of the housing 10. When the button 70 is pressed, these spline teeth are disengaged allowing the drive sleeve 40 to rotate relative to the housing 10. Clutch spring 130 biases the drive sleeve 40 into a position engaging with its teeth the teeth of the housing. A further splined tooth interface with the number sleeve 60 is not engaged during dialing, but engages when the button 70 is pressed, preventing relative rotation between the drive sleeve 40 and number sleeve 60 during dispense. In a preferred embodiment this interface comprises inwardly directed splines on a flange on the inner surface of the number sleeve 60 and a ring of radially extending outer splines of drive sleeve 40. These corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

A further interface of the drive sleeve 40 comprises a ring of ratchet teeth located at the proximal end face of drive sleeve 40 and a ring of corresponding ratchet teeth on the clutch plate 120.

The driver 40 has a threaded section providing a helical track for the nut 50. In addition, a last dose abutment or stop is provided which may be the end of the thread track or preferably a rotational hard stop for interaction with a corresponding last dose stop of nut 50, thus limiting movement of the nut 50 on the driver thread. At least one longitudinal spline of the driver 40 engages a corresponding track of the lead screw 30.

The last dose nut 50 is located between the number sleeve 60 and the drive sleeve 40. It is rotationally constrained to the number sleeve 60, via a splined interface. It moves along a helical path relative to the drive sleeve 40, via a threaded interface, when relative rotation occurs between the number sleeve 60 and drive sleeve 40 which is during dialing only. As an alternative, the nut 50 may be splined to the driver 40 and threaded to the number sleeve 60. A last dose stop is provided on nut 50 engaging a stop of drive sleeve 40 when a dose is set corresponding to the remaining dispensable amount of medicament in the cartridge.

The dose indicator or number sleeve 60 is a tubular dose setting element. The number sleeve 60 is rotated during dose setting (via dose selector 80) and dose correction by the user and during dose dispensing by torsion spring 90. The number sleeve 60 is constrained to the housing 10 by a snap engagement to allow rotation but not translation. The number sleeve 60 comprises an annular recess or groove near its distal end which engages a corresponding bead on an inner surface of the housing 10. The number sleeve 60 is marked with a sequence of numbers, which are visible through the gauge element 110 and the opening 11*a* in the housing 10, to denote the dialed dose of medicament. Further, the number sleeve 60 has a portion with an outer thread 61 engaging the gauge element 110. End stops may be provided at the opposite ends of thread to limit relative movement with respect to the gauge element 110. If these end stops are provided, the number sleeve 60 and the gauge element 110 define a zero position ('at rest') and a maximum dose position. As an alternative, the limiter 100 and the gauge element 110 may define a zero position ('at rest') and a maximum dose position as explained below.

Clutch features which have the form of a ring of splines are provided inwardly directed on number sleeve 60 for engagement with splines of the button 70 during dose setting and dose correction. A clicker arm may be provided on the outer surface of number sleeve 60 which interacts with the drive sleeve 40 and the gauge member 110 for generating a feedback signal. In addition, the number sleeve 60 is rotationally constrained to the nut 50 and to the clutch plate 120 via a splined interface comprising at least one longitudinal spline. Further, number sleeve 60 comprises an interface for attachment of the torsion spring 90. The number sleeve 60 has a proximal portion provided with axially extending splines 62 engaging corresponding splines 101 of limiter 100. Thus, limiter 100 is permanently rotationally constrained to number sleeve 60 whereas a relative axial movement between number sleeve 60 and limiter 100 is permitted.

The button 70 which forms the proximal end of the device is permanently splined to the dose selector 80. A central stem extends distally from the proximal actuation face of the button 70. The stem is provided with a flange carrying the splines for engagement with splines of the number sleeve 60 when the button 70 is not pressed, but this spline interface is disconnected when the button 70 is pressed. The button 70 also has a discontinuous annular skirt with triangular shaped teeth. When the button 70 is pressed, triangular shaped teeth on the button 70 engage with teeth on the housing 10, preventing rotation of the button 70 (and hence the dose selector 80) during dispense. These splines disengage when the button 70 is released, allowing a dose to be dialed. Further, a ring of ratchet teeth may be provided on the inner side of the button flange for interaction with a clicker feature of clutch plate 120. The button 70 is axially constrained to limiter 100, for example by snap engagement, but may be allowed to rotate relative to the limiter 100.

The dose selector 80 is axially constrained, but free to rotate with respect to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end by a hook to the housing 10 and at the other end to the number sleeve 60. The torsion spring 90 is located inside the number sleeve 60 and surrounds a distal portion of the drive sleeve 40. The torsion spring 90 is pre-wound upon assembly, such that it applies a torque to the number sleeve 60 when the mechanism is at zero units dialed. The action of rotating the dose selector 80, to set a dose, rotates the number sleeve 60 relative to the housing 10, and charges the torsion spring 90 further.

The cartridge is received in cartridge holder 20. The cartridge may be a glass ampoule having a moveable rubber bung at its proximal end. The distal end of cartridge is provided with a pierceable rubber seal which is held in place by a crimped annular metal band. In the embodiment depicted in the Figures, the cartridge is a standard 1.5 ml cartridge. The device is designed to be disposable in that the cartridge cannot be replaced by the user or health care professional. However, a reusable variant of the device could be provided by making the cartridge holder 20 removable and allowing backwinding of the piston rod 30 and the resetting of nut 50.

Figure 5:
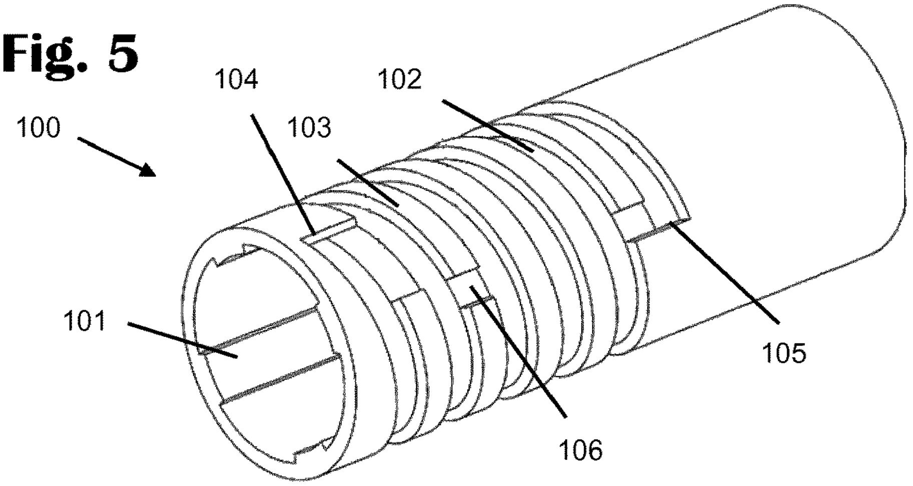
FIG. 5 shows in a perspective view a component of the device of FIG. 1.

The limiter 100 is a tubular element having axially extending splines 101 on its inner surface engaging splines 62 of the number sleeve. The outer surface of the limiter 100 is provided with a helically extending path, i.e. a thread form, defined by a helical groove 102. The thread turns of the groove 102 are spaced from each other by a helical rib 103. The lead of the thread turns on the limiter 100 is essentially the same as the lead of thread 61 of number sleeve 60. In the embodiment of FIGS. 3 and 5, the groove 102 is provided with a distal end stop 104 and a proximal end stop 105. The end stops 104, 105 are rotational hard stops.

The helical rib 103 is discontinuous with clearances 106 provided between sections in which the rib 103 is present. The groove 102 defines a track with narrow sections limiting relative axial movement between the track and the blocking feature 112 in sections where the rib 103 is present on both sides of the groove and wide sections permitting relative axial movement between the track and the blocking feature 112 in sections where a clearance 106 is provided. In the embodiment of FIGS. 3 and 5 a first larger clearance 106 is arranged adjacent distal stop 104 (minimum dose stop), a smaller clearance 106 is provided in a middle portion of rib 103 and a third clearance 106 is provided adjacent proximal stop 105 (maximum dose stop). The quantity, size and location of the clearances 106 are shown in the Figures as an example and may be varied. In the embodiment of FIGS. 1 to 5 the wide sections of the track which are defined by the presence of a clearance 106 on the proximal side of the groove 102 are positioned near the zero dose stop 104, a little bit more than one full rotation after the zero dose stop 104 and near the maximum dose stop 105. A blocking feature 112 of gauge element 110 engages groove 102 of limiter 100.

Figures 3A, 3B:
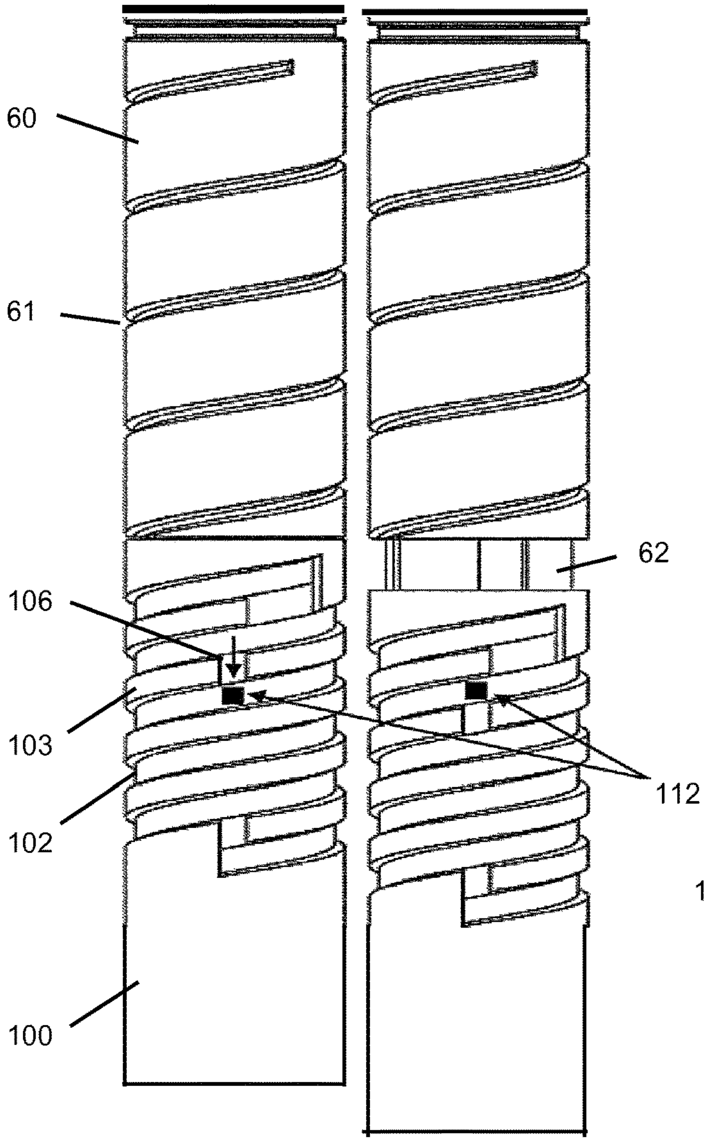
FIG. 3*a* shows two components of the device of FIG. 1 in the dose setting state.
FIG. 3*b* shows two components of the device of FIG. 1 in a dose dispensing state.
Figure 4:
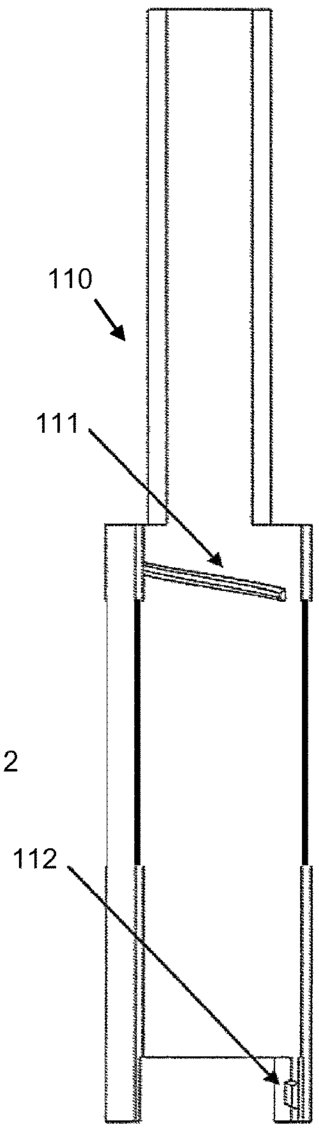
FIG. 4 shows a further component of the device of FIG. 1.

The gauge element 110 is constrained to prevent rotation but allow translation relative to the housing 10 via a splined interface. As depicted in FIG. 4 the gauge element 110 may comprise a portion in the form of e.g. a half shell (left side in FIG. 4) and a band-like portion extending in the distal direction. In FIG. 1, the half shell portion is visible through window 11*a* and the band-like portion is visible through window 11*b*. The gauge element 110 has a helical feature 111 on its inner surface which engages with the helical thread cut 61 in the number sleeve 60 such that rotation of the number sleeve 60 causes axial translation of the gauge element 110. If the thread 61 of the number sleeve 60 is provided with rotational end stops, this helical feature 111 on the gauge element 110 may also create stop abutments against the end of the helical cut 61 in the number sleeve 60 to limit the minimum and maximum dose that can be set. In the embodiment depicted in FIGS. 3 and 5, the minimum and maximum dose that can be set is limited by blocking feature 112 of gauge element 110 engaging distal and proximal stops 104, 105, respectively. As shown in FIGS. 3*a* and 3*b*, the blocking feature 112 has dimensions permitting that the blocking feature 112 is guided within groove 102 between portions of rib 103. Further, clearances 106 have dimensions permitting the blocking feature 112 to be displaced from one thread turn to the adjacent thread turn when the limiter is moved axially relative to gauge element 110.

The gauge element 110 has a partially cylindrical form, with a central aperture or window and two surfaces extending on either side of the aperture. The gauge element 110 is preferably not transparent and thus shields or covers the number sleeve 60, whereas the aperture or window allows viewing a portion of the number sleeve 60. Further, gauge element 110 may have a cam and a recess interacting with the clicker arm of the number sleeve 60 at the end of dose dispensing.

The clutch plate 120 is a ring-like component. The clutch plate 120 is splined to the number sleeve 60 via splines. It is also coupled to the drive sleeve 40 via a ratchet interface. The ratchet provides a detented position between the number sleeve 60 and drive sleeve 40 corresponding to each dose unit, and engages different ramped tooth angles during clockwise and anti-clockwise relative rotation. A clicker arm may be provided on the clutch plate 120 for interaction with ratchet features of the button 70.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when ‘at rest’ it is further reacted through the dose selector 80 to the housing 10. The spring force ensures that the ratchet interface between drive sleeve 40 and clutch plate 120 is always engaged. In the ‘at rest’ position, it also ensures that the button splines are engaged with the number sleeve splines, and the drive sleeve teeth are engaged with teeth of the housing 10.

With the device in the ‘at rest’ condition as shown in FIGS. 1 and 2, the blocking feature 112 is positioned against its zero dose abutment 104 with the limiter 100 and the button 70 is not depressed. Dose marking ‘0’ on the number sleeve 60 is visible through the window 11*a* of the housing 10 and gauge element 110, respectively. The torsion spring 90, which has a number of pre-wound turns applied to it during assembly of the device, applies a torque to the number sleeve 60 and is prevented from rotating by the zero dose abutment.

The user selects a dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement 61, 111 thereby showing the value of the dialed dose. The gauge element 110 has surfaces either side of the window area which cover the numbers printed on the number sleeve 60 adjacent to the dialed dose to ensure only the set dose number is made visible to the user.

A specific feature is the inclusion of a visual feedback feature in addition to the discrete dose number display typical on devices of this type. The distal end of the gauge element 110 creates a sliding scale through the small window 11*b* in the housing 10. As an alternative, the sliding scale could be formed using a separate component engaged with the number sleeve 60 on a different helical track.

As a dose is set by the user, the gauge element 110 translates axially, the distance moved is proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting coloured component underneath. Alternatively, the revealable element may be printed with coarse dose numbers or other indices to provide more precise resolution. In addition, the gauge display simulates a syringe action during dose set and dispense.

The drive sleeve 40 is prevented from rotating as the dose is set and the number sleeve 60 rotated, due to the engagement of its splined teeth with teeth of the housing 10. Relative rotation must therefore occur between the clutch plate 120 and drive sleeve 40 via the ratchet interface.

The user torque required to rotate the dose selector 80 is a sum of the torque required to wind up the torsion spring 90, and the torque required to overhaul the ratchet interface. The clutch spring 130 is designed to provide an axial force to the ratchet interface and to bias the clutch plate 120 onto the drive sleeve 40. This axial load acts to maintain the ratchet teeth engagement of the clutch plate 120 and drive sleeve 40. The torque required to overhaul the ratchet in the dose set direction is a function of the axial load applied by the clutch spring 130, the clockwise ramp angle of the ratchet teeth, the friction coefficient between the mating surfaces and the mean radius of the ratchet interface.

As the user rotates the dose selector 80 sufficiently to increment the mechanism by one increment, the number sleeve 60 rotates relative to the drive sleeve 40 by one ratchet tooth. At this point the ratchet teeth re-engage into the next detented position. An audible click is generated by the ratchet re-engagement, and tactile feedback is given by the change in torque input required.

Relative rotation of the number sleeve 60 and the drive sleeve 40 is allowed. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface between the number sleeve 60 and drive sleeve 40 is repeated for each dose increment. Additional energy is stored within the torsion spring 90 for each dose increment and audible and tactile feedback is provided for each increment dialed by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

During dose setting, the blocking feature 112 is guided in groove 102 between portions of rib 103. This may cause a relative axial movement of the limiter 100 with respect to the number sleeve 60 if the lead of threads 61 and 102 is not identical. If the user continues to increase the selected dose until the maximum dose limit is reached, the blocking feature 112 engages with maximum dose abutment 105 on the limiter 100. This prevents further rotation of the limiter 100, number sleeve 60, clutch plate 120 and dose selector 80.

Depending on how many increments have already been delivered by the mechanism, during selection of a dose, the last dose nut 50 may contact its last dose abutment with stop face of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface between the clutch plate 120 and drive sleeve 40 in the anti-clockwise direction. When the ratchet is overhauled, anti-clockwise rotation occurs in the number sleeve 60 (via the clutch plate 120 and torsion spring 90), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction. As noted above, the limiter 100 is axially constrained to the button 70. Thus, activation of the mechanism, i.e. initiation of dose dispensing, requires a distal movement of the limiter 100 that corresponds to the axial movement of button 70. However, axial movement of the limiter 100 is limited if blocking feature 112 of the gauge element 110 engages a narrow section of the track formed by groove 102 and rib 103 because the gauge element 110 is coupled to the housing 10 via number sleeve 60. In other words, although gauge element 110 travels axially during dose setting, the position of the gauge element 110 with respect to the housing 10 is fixed as dose setting is stopped due to the helical feature 111 on the gauge element 110 engaging the helical cut 61 of the number sleeve which is axially constrained to the housing 10. On the other hand, if blocking feature 112 is in a wide section of the track, i.e. a section with clearance 106, the limiter 110 may be displaced relative to the gauge element 110 with the blocking feature 112 passing from one thread turn into an adjacent thread turn, thus allowing depressing of the button 70.

Referring now to FIGS. 3*a* and 3*b*, the limiter 100 may be connected to the button 70 with a joint that permits relative rotation, but not axial movement. When the button 70 is pushed in the needle direction (to dispense a dose), the force is transmitted to the limiter 100 to try to move it proximally relative to the gauge element 110 and number sleeve 60 components. If the blocking feature 112 of the gauge element 110 is located in a region where it abuts the distal side of a portion of the blocking rib 103 of the limiter 100, then the limiter 100 cannot be moved distally, meaning that the button 70 cannot move distally relative to the number sleeve 60 or gauge element 110. This in turn means that the clutch between the button 70 and number sleeve 60 does not disengage and so the dose cannot be dispensed.

In FIG. 3*a* the components are arranged in a position where the blocking feature 112 on the gauge element aligns on the distal side with a gap or clearance 106 in the blocking rib 103, i.e. the blocking feature 112 is in a wide section of the track. For example, this might be a desired therapeutic dose. In this position, it is possible to displace the limiter 100 in the distal direction relative to the gauge element 110 and number sleeve 60 and so a dose can be delivered. FIG. 3*b* shows the limiter 100 displaced distally with respect to the number sleeve 60, the gauge element 110 and the housing 10, such that the blocking feature 112 has moved within the wide section of the track from one thread turn to the adjacent proximal thread turn.

When the blocking feature 112 is engaged on the distal side of the blocking rib 103, the user is prevented from dispensing a dose as described above. In this condition, axial force applied by the user is transmitted from the button 70 via limiter 100 to the blocking feature 112 on the gauge element 110 and then directly on to the number sleeve 60 and the housing 10. Due to the relatively short, direct load path between the blocking features, the blocking action is strong and positive (i.e. there should be little flexibility in this stop, which if present could confuse users).

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Triangular teeth on the button 70 engage with teeth on the housing 10, preventing rotation of the button 70 (and hence the dose selector 80) during dispense. As the button 70 is stationary during dispense, it can be used in the dispense clicker mechanism. A stop feature in the housing 10 may limit axial travel of the button 70 and reacts any axial abuse loads applied by the user, reducing the risk of damaging internal components.

The clutch plate 120 and drive sleeve 40 travel axially with the button 70. This engages the splined tooth interface between the drive sleeve 40 and number sleeve 60, preventing relative rotation between the drive sleeve 40 and number sleeve 60 during dispense. The splined tooth interface between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment stops the mechanism.

Tactile feedback during dose dispense may be provided via the compliant cantilever clicker arm integrated into the clutch plate 120. This arm interfaces radially with ratchet features on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines between the drive sleeve 40 and housing 10, preventing further rotation and stopping dose delivery. This only occurs if the button 70 is released in a location where the limiter 100 allows the button 70 to return to the 'at rest' position. If the button 70 is released with the limiter 100 located in a blocked position, then the button 70 is prevented from returning.

During delivery of a dose, the drive sleeve 40 and number sleeve 60 rotate together, so that no relative motion in the last dose nut 50 occurs. The last dose nut 50 therefore travels axially relative to the drive sleeve 40 during dialing only. As the dose is dispensed, the number sleeve 60 and the limiter 100 spin against the housing 10, whilst the gauge element 110 travels axially (with no rotation) back towards the distal needle-end of the device. The limiter 100 is moved proximally by the user pressing on the button 70, resulting in the blocking feature 112 running along the proximal side of the blocking rib 103.

Once the delivery of a dose is stopped, by the distal end of the helical feature 11 contacting the distal end of thread 61, the user may release the button 70, which will re-engage the spline teeth between the drive sleeve 40 and housing 10. The mechanism is now returned to the 'at rest' condition. Due to the clearance 106 near the minimum dose stop 104 blocking element 112 returns into its original position, i.e. it returns to its original thread turn passing through the clearance 106 of rib 103.

At the end of dose dispensing, additional audible feedback may be provided in the form of a 'click', distinct from the 'clicks' provided during dispense, to inform the user that the device has returned to its zero position via the interaction of the clicker arm on the number sleeve 60 with the ramp on the drive sleeve 40 and the cam and the recess on the gauge element 110. This embodiment allows feedback to only be created at the end of dose delivery and not created if the device is dialed back to, or away from, the zero position.

Because the features that define the deliverable dose values are all formed on the limiter 100, the device can be configured for different applications very easily by changing only one component. Similarly, because the dose limitating features do not protrude beyond the basic 'envelope' of the limiter 100, it should also be straightforward to assemble a wide range of different device configurations using common automated assembly equipment.

Although the ribs 103 are depicted as having proximal and distal side surfaced being mainly perpendicular to the axis I of the device, other embodiments may have a ramp-like configuration of the ribs with a steeper distal face and a slanted proximal face. In addition, or as an alternative, the blocking features may have a ramp-like configuration of the ribs with a steeper proximal face and a slanted distal face. This facilitates returning of the blocking feature into the adjacent distal thread turn even if the blocking feature is in a narrow section of the track. This may be required to pause or stop dose dispensing.

Figures 6, 7, 8, 9:
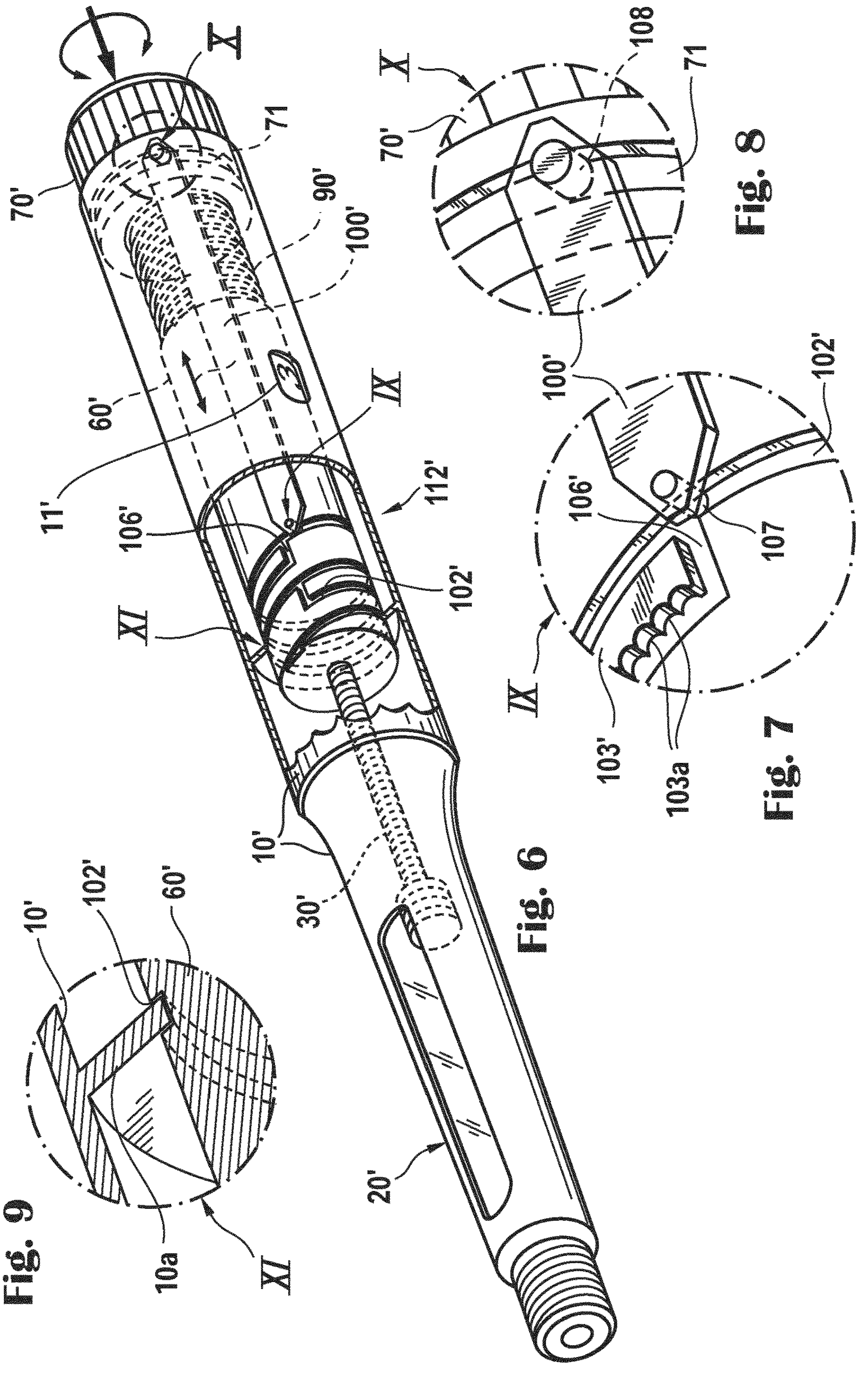
FIG. 6 shows a perspective view of a drug delivery device according to a second embodiment.
FIG. 7 shows enlarged detail VII of FIG. 6.
FIG. 8 shows enlarged detail VIII of FIG. 6.
FIG. 9 shows enlarged detail IX of FIG. 6.

A second embodiment is shown in FIGS. 6 to 9. The device comprises an outer housing 10', a cartridge holder 20', a piston rod 30', a dose selecting element 60' and a button 70' or trigger. The dose selecting element 60' is in threaded engagement with the housing 10' by means of a helical housing rib **10*a* being guided in a female helical thread form 102' of the dose selecting element as shown in FIG. 9 in more detail. Thus, the dose selecting element is axially displaced relative to the housing upon rotation of the dose selecting element. A window 11' is provided in the housing 10' such that a scale provided e.g. on the outer surface of the dose selecting element 60' is visible in the window 11'**.

Further, a track 112' is provided at the distal end of the dose selecting element 60'. The track 112' may be a unitary component part of the dose selecting element or may be axially and rotationally constrained to the dose selecting element. The track 112' comprises a helical groove 102' defined by helical ribs 103'. The pitch and lead of the helical groove 102' correspond to the pitch and lead of the threaded interface between the dose selecting element 60' and the housing 10'. A clearance 106' is provided at two positions of the track 112', thereby defining wider sections of the track 112' (of groove 102'), while the remaining sections of groove 102' define narrower sections of the track 112'.

A limiter 100' in the form of an elongate pusher extends and is axially guided within the housing 10'. Limiter 100' is coupled with its proximal end to the button 70' and with its distal end to the track 112'. FIG. 7 shows in more detail that a pin-like feature 107 of the limiter 100' engages groove 102' of the track 112' at the distal end of the limiter. FIG. 8 shows that a pin-like feature 108 of the limiter engages a circumferentially extending groove 71 of the button 70'. Thus, button 70' may be rotated relative to the limiter 100', e.g. during dose setting, but transmits axial movement of the button 70' to the limiter 100'.

In the embodiment of FIG. 7, the distal face of rib 103' is shown serrated. This serration **103*a* is mated with the pin 107 such that the friction between track 112' and limiter 100' is increased if the pin 107 abuts the distal face of rib 103'. The serration may be formed such that relative rotation between the pin 107 and the distal face of rib 103'** is substantially, preferably fully, prevented.

In use of the device a dose is set by rotation of button 70' which causes concurrent rotation of the dose selecting element 60'. Rotation of the dose selecting element 60' results in axial displacement of the dose selecting element 60' due to its threaded engagement with the housing 10'. Button 70' is not axially displaced during dose setting such that limiter 100' is not moved axially, either. The distal end of limiter with pin 107 is guided in groove 102' of the track 112' of dose selecting element 60'. As long as pin 107 is guided in the narrow section of groove 102', i.e. if the pin 107 is not in line with a clearance 106', axial movement of the button 70' (which is required to initiate dose dispensing) is prevented due to the interaction with limiter 100'.

If a dose has been set which corresponds to a predefined dose, the pin 107 is aligned with a clearance 106', that is a wider section of groove 102'. In this position, a user may push button 70' to start dose dispensing. During this axial movement of limiter 100' and button 70', pin 107 moves through clearance 106' from a proximal thread form of groove 102' into the distally adjacent thread form. Actuation of the button 70' may e.g. release a torsion spring 90' for driving the piston rod 30'. This may also cause the dose selecting element 60' to wind back together with the limiter 100' being guided in track 112'.

If a user releases button 70' prior to having the previously set dose fully dispensed, a not shown spring may bias the button in the proximal direction. The button 70' entrains limiter 100' axially such that pin 107 contacts the serrated distal face **103*a* of rib 103'. Due to the interaction of the serrated face with pin 107 (and/or due to friction) further rotation of the blocking feature 112', and thus the dose selecting element 60', is stopped by limiter 100'. This in turn stops dose dispensing. Dose dispensing may be continued by actuation of the button 70' which releases the engagement (or friction) of pin 107 with the serrated face 103*a* of rib 103'**.

In the embodiment of FIGS. 6 to 9, groove 102' being the track 112' is a slide way for a slide block formed by pin 107 which is the blocking feature. In addition, groove 102' is the thread form engaging helical housing rib **10*a*. In other words, the slide way for the limiter mechanism may be identical with a thread provided for interaction of further components of the drug delivery device, preferably the thread guiding the dose selecting element and/or a number sleeve. This may have the benefit of reducing the space required for the limiter mechanism. On the other hand, in the embodiment of FIGS. 1 to 5, the slide way formed by groove 102, i.e. the track, and the slide block formed by blocking feature 112 are provided separate and spaced from the thread 61, 111 guiding the dose selecting element 60 and the gauge element 110** with respect to each other. In other words, the slide way for the limiter mechanism may be separate from a thread provided for interaction of further components of the drug delivery device, preferably the thread guiding the dose selecting element and/or a number sleeve. As a further alternative, the slide way and the slide block of the limiter mechanism may be located close to, e.g. overlapping with, a thread provided for interaction of further components of the drug delivery device, preferably the thread guiding the dose selecting element and/or a number sleeve. For example, a slide way (track) of the limiter mechanism may be provided such that it is interposed between the female thread guiding the dose selecting element and/or a number sleeve, i.e. a groove of the limiter mechanism is provided adjacent to a groove of the further thread guiding the dose selecting element and/or a number sleeve. Again, this may have the benefit of reducing the space required for the limiter mechanism.

The first embodiment of FIGS. 1 to 5 or the second embodiment shown in FIGS. 6 to 9 may further improved by a mechanism explained in detail below with regard to FIGS. 10 to 15, which increases the likelihood of stopping delivery of a dose when the button is released part way through dispense of the dose and continue delivery by pressing the injection button again. All embodiments described with reference to FIGS. 10 to 26*b* in the following are derived from the embodiment depicted in FIGS. 1 to 5 but the described features may be transferred to the embodiment shown in FIGS. 6 to 9 accordingly.

Figure 10:
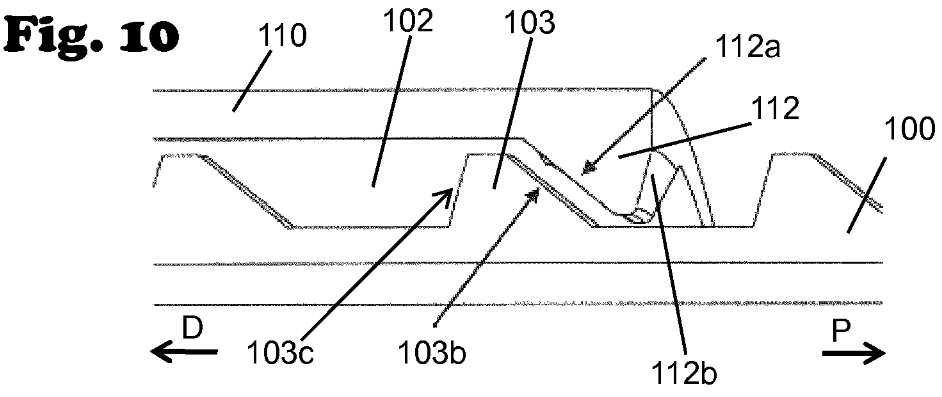
FIG. 10 shows an enlarged detail of a longitudinal section of a drug delivery device according to a third embodiment.
Figure 11:
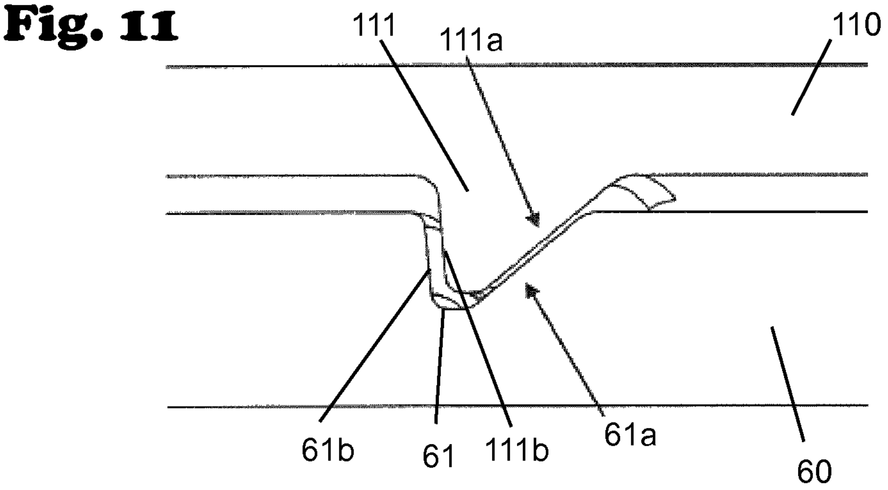
FIG. 11 shows an enlarged detail of a longitudinal section of a drug delivery device according to a fourth embodiment.

During dispense, if the user stops applying force to the button 70 in the first embodiment shown in FIGS. 1 to 5 the limiter 100 is pushed proximally (the proximal direction is depicted in FIG. 10 and the following Figures by arrow P) by the clutch spring 130. If this occurs in a region where the blocking feature 112 aligns with one clearance 106 in rib 103 the limiter 100 (and button 70) can return to their dialing positions and dispense will stop. However, if the application or force is removed from the button 70 when the blocking feature 112 abuts the distal side of the rib 103 the return of the limiter 100 is blocked by the gauge element 110 and one of the three following scenarios could occur.

a) The device continues to dispense the entire dialed dose.

b) The device continues to dispense until a clearance 106 in the rib 103 is reached, at which point translation of the limiter 100 is no longer blocked by the gauge element 110 and it can return to its dialing position.

c) The additional friction in the system (caused by the interaction of the gauge element 110 and the limiter 100) is sufficient to stop dispense of the device.

The embodiments described below are designed to improve the probability of scenario c) occurring which is potentially advantageous for user safety and control. This in particular is because upon pausing delivery, the user will be unable to adjust the dose from the preselected value, but will be able to continue delivery by pressing the button 70 again.

In a first embodiment shown in FIG. 10 the flank angle of the proximal face 103*b* of rib 103 and the flank angle of the distal face 112*a* of the blocking feature 112 of the gauge element 110 is altered and, in particular, made shallower so that the reaction force at the interface between the two abutting surfaces 103*b*; 112*a* increases when they are brought into contact by the force of the clutch spring 130. This effect relies on the regular stiffness of the two elements creating a so-called wedging effect. Because reaction force and friction force are directly proportional the increase in reaction force due to this wedging effect creates a proportional increase in friction which acts to hold dispense. As one can derive from FIG. 10 showing a longitudinal section through the limiter 100 and the gauge element 110 the blocking element 112 and each rib 103 forming the track 102 of the limiter 100 comprise a saw-tooth cross-sectional form wherein one flank has a shallower angle than the other. In this case, the proximal face 103*b* of rib 103 has a shallower angle then the distal face 103*c*. Accordingly, the distal face 112*a* of the blocking feature 112 has a shallower angle than the proximal face 112*b*. If the dispense is stalled the distal face 112*a* of the blocking feature 112 abuts to the proximal face 103*b* of the blocking rib 103 exhibiting a strong friction force. The angle difference between the two flanks of the blocking feature 112 or the rib 103 amounts, for example, to a value between 10° and 60°. The same effect can be achieved in an alternative embodiment by making only one of the mating faces of the limiter rib or blocking feature shallow. The reason that both are made shallow is that this increases the strength of the features when subjected to load in the blocking condition.

The same effect and advantage is received when, in another embodiment, the interface between the gauge element 110 and the number sleeve 60 is taken into account. If the button 70 is released mid-dispense, the clutch spring 130 forces the proximal face 111*a* of the rib forming the helical feature 111 onto the proximal side of the thread 61 formed as a groove (see FIG. 11). Accordingly, the proximal face 61*a* of the groove 61 is shallower than the distal face 61*b* of the thread 61 and the proximal face 111*a* of the helical feature 111 is shallower than the distal face 111*b*. This creates a proportional increase in friction leading to stall the dispense movement if the button 70 is released as well.

Figure 12:
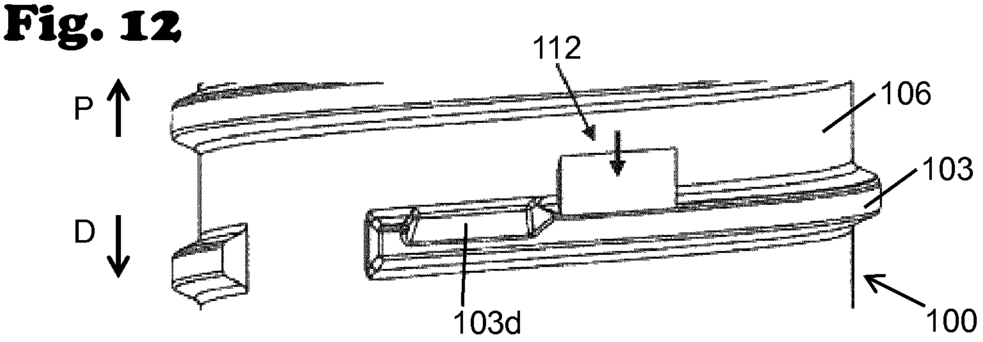
FIGS. 12 & 13 show an enlarged detail of a perspective view of a drug delivery device according to a fifth embodiment when dose dispense is stalled.
Figure 13:
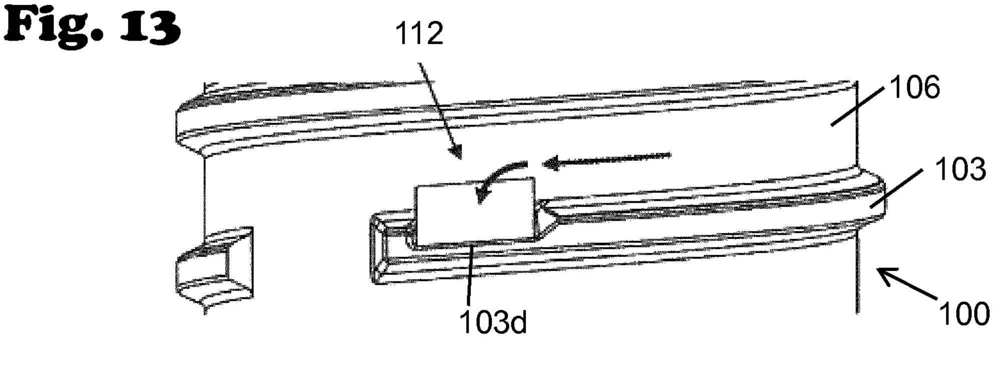

In another embodiment at least one detent 103*d* is provided at the proximal side of rib 103 of the limiter 100 (see FIG. 12). Preferably a plurality of detents 103*d* are arranged, preferably accommodated at the proximal side of rib 103 at regular intervals, to aid in retarding the relative motion of the limiter 100 and the gauge element 110. In an embodiment, the detent 103*d* comprises an approximately rectangular base area forming an indentation within the rib 103 and is surrounded by tapered edges. During dialing or dispense, these detents 103*d* are sized such that the blocking feature 112 of the gauge element 110 runs in clearance of them. However, if the user ceases to apply force to the button 70 during dispense, the blocking rib 103 is forced proximally into the blocking feature 112, causing it to come into contact with one of the detents 103*d* (see FIG. 13). This contact will act to hold the relative motion between the gauge element 110 and the limiter 100 and thus stop dispense.

Figure 14:
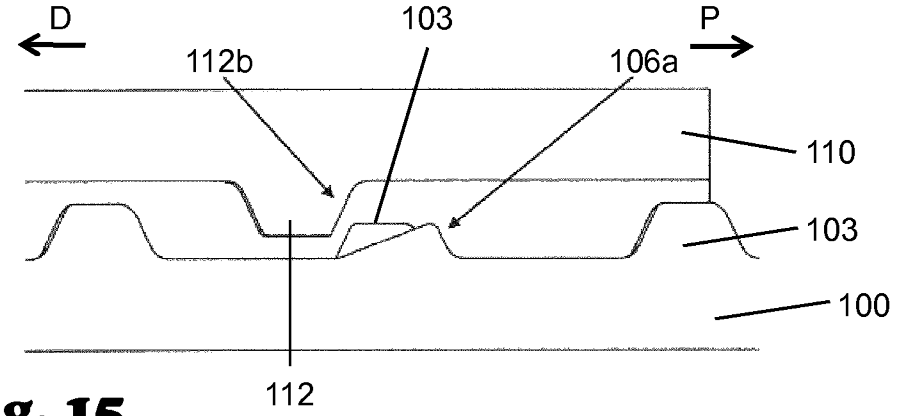
FIG. 14 shows an enlarged detail of a longitudinal section of a drug delivery device according to a sixth embodiment in a dose setting state.
Figure 15:
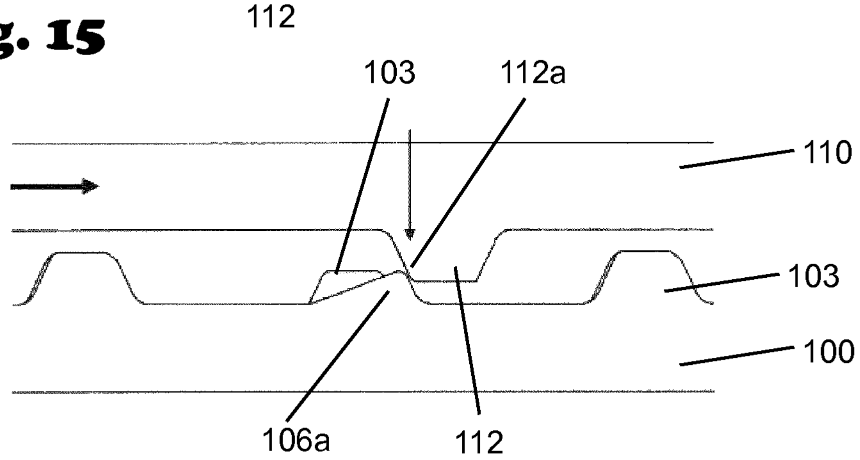
FIG. 15 shows the view and embodiment of FIG. 14 in a dose dispensing state.
Figure 16A:
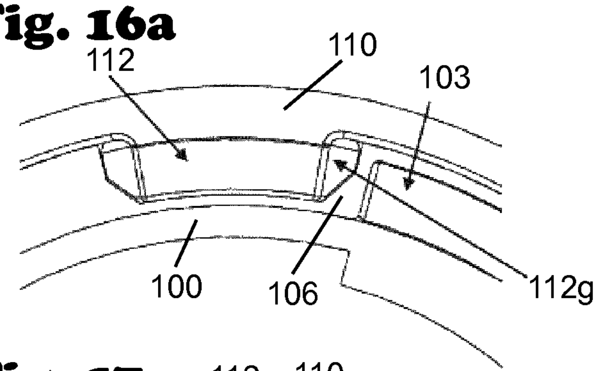
FIGS. 16*a* & 16*b* show an enlarged detail of a cross section of a drug delivery device according to a seventh embodiment in a nominal dispense position.
Figure 16B:
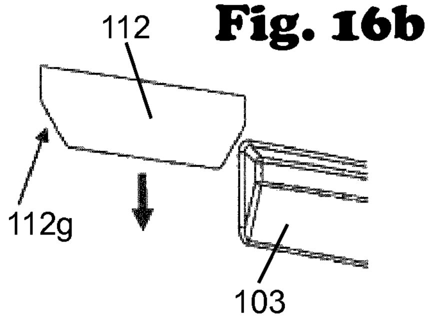
Figure 17A:
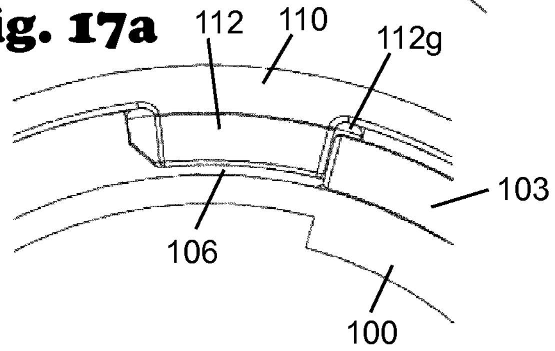
FIGS. 17*a* & 17*b* show an enlarged detail of a cross section of the drug delivery device according to the seventh embodiment in a tolerance extreme position.
Figure 17B:
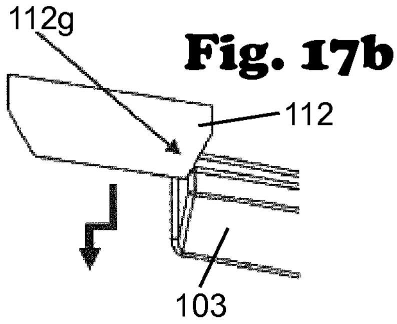
Figure 18:
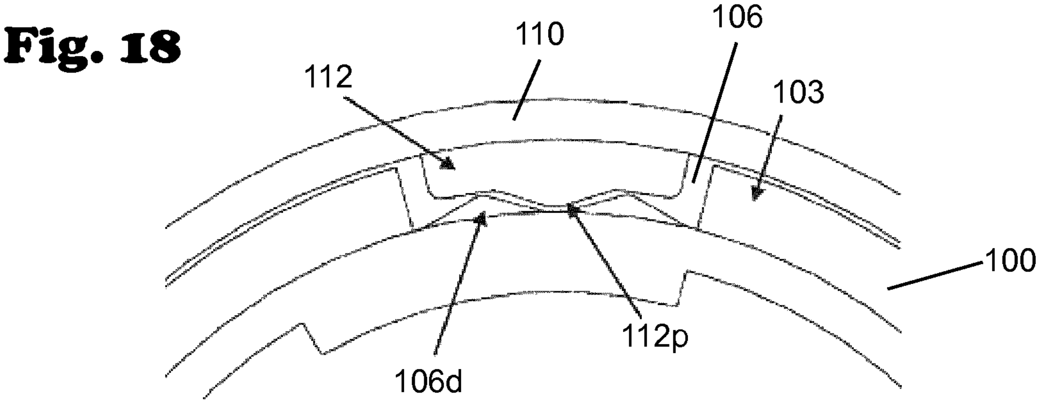
FIG. 18 shows an enlarged detail of a cross section of a drug delivery device according to an eighth embodiment in a nominal dispense position.
Figure 19:
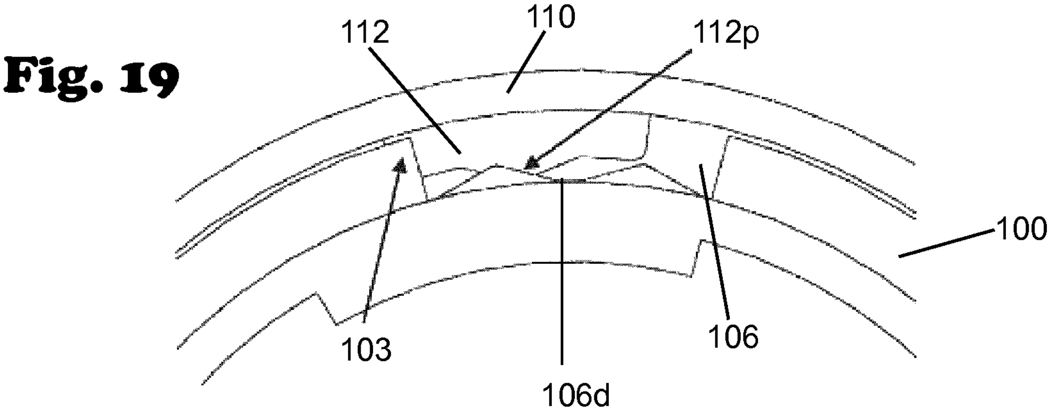
FIG. 19 shows an enlarged detail of a cross section of the drug delivery device according to the eighth embodiment in a dispense position at extreme of tolerances.

The embodiment shown in a longitudinal section in FIGS. 14 and 15 uses ramps on the limiter 100 to create a one-way commit feature. One commit ramp 106*a* is formed in the clearance 106 of the blocking rib 103 so that, in order to initiate a dispense event, the blocking feature 112 is forced over and passes this ramp 106*a* when the limiter 100 moves in distal direction (see arrow D). The ramps are axially asymmetric, meaning greater force is required to move the blocking feature 112 past the ramp 106*a* in distal direction. Therefore, as shown in FIG. 15 if the button 70 is released during dispense the ramp 106*a* acts to stop the blocking feature 112 and thereby the gauge element 110 returning to its dialing position. The ramp 106*a* comprises therefore a shallower flank on its distal side than on its proximal side. The crown line of the ramp 106*a* runs in a direction perpendicular to the axial direction (axis I) and comprises a smaller inclination on the distal side than on the proximal side.

All features described above for supporting safe dispense of the drug when the pressure applied to the button 70 is released may be combined. The features may analogously be used for the embodiment shown in FIGS. 6 to 9 as well.

The embodiments described in FIGS. 16*a*, 16*b*, 17*a*, 17*b*, 18, 19 and 20 improve the alignment of the gauge element 110 and limiter 100 of the device described in FIGS. 1 to 5 above. The key objective of the alignment feature is to ensure that the blocking and dispensing functions of the device are unaffected at extremes of component tolerances and in particular to achieve acceptable blocking strength.

The features described below may similarly be used for other devices as well, in particular the device of FIGS. 6 to 9 as the features are designed to address a device mechanism which displays a relative helical movement of a feature with respect to a secondary component.

During dialing the blocking feature 112 of the device shown in FIGS. 1 to 5 travels along a helical path 102 between the blocking ribs 103. When the device button 70 is pushed in the distal direction in order to dispense a dose, this force is transmitted to the limiter 100 which tries to move distally relative to the gauge element 110. If the dialed dose is equal to a desired therapeutic dose, in this position it is possible to displace the limiter 100 in the distal direction relative to the gauge element 110 leading to dose delivery. However, the position of the blocking feature 112 relative to the limiter 100 is dictated by a chain of other components, each with their own associated manufacturing tolerances. The cumulative effect of these component tolerances could foreseeably result in the limiter 100 and gauge element 110 being rotationally misaligned (from their nominal positions shown in FIG. 3*a*) to the point where the blocking feature 112 abuts a region of the blocking rib 103 despite the device having been dialed to a permissible dose. The embodiments of devices described with regard to FIGS. 16*a* to 20 make it possible to control the alignment of the limiter 100 and the gauge element 110 such that the blocking and dispensing functions of the device are supported even at extremes of component tolerances.

In the embodiment depicted in FIGS. 16*a* to 17*b* the blocking feature 112 comprises lead-in ramps 112*g* formed on both faces of the projection 112 in the circumferential direction. The lead-in ramps 112*g* form slanted or tapered faces at the inner ends of the blocking feature 112. If the tolerances are small, the blocking feature 112 moves through the clearance 106 without touching the blocking rib 103 in order to initiate dispense (see FIGS. 16*a* and 16*b*). At extremes of tolerance, the lead-in ramps 112*g* at the blocking feature 112 rotationally overlap with the blocking rib 103 of the limiter 100 even if the correct dose is dialed. When a user initiates dispense by pushing the button 70, the limiter 100 translates axially so that the blocking feature 112 and the rib 103 come into contact. As it is shown in FIGS. 17*a* and *b* the blocking feature lead-in ramp 112*g* acts to correct the rotational position of the gauge element 110 and the limiter 100 so that dispense can occur, using the available rotational clearances between components in the tolerance chain.

Figure 20:
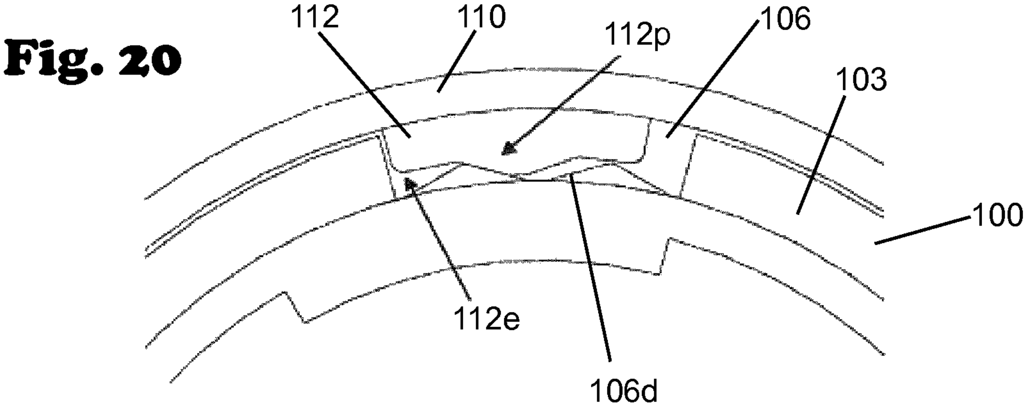
FIG. 20 shows an enlarged detail of a cross section of the drug delivery device according to the eighth embodiment in a corrected dispense position.

In another embodiment the clearance 106 comprises a positive detent 106*d* or groove formed by two ribs extending in axial direction. This means the base line of the detent extends in the axial direction. The detent comprises a triangular cross section. Correspondingly, the blocking feature 112 comprises a meshing alignment ramp 112*p* which also extends in the axial direction, i.e. its crown line extends in the axial direction. As one can derive from the FIGS. 18 to 20 the elevation of the alignment ramp 112*p* and the depression of the detent 106*d* are in the radial direction. In a nominal dispense position shown in FIG. 18 the alignment ramp 112*p* at the blocking feature 112 of the gauge element 110 is flanked by the flanks of the detent 106*d* and the alignment features 112*p* and 106*d* are aligned. If, due to manufacturing tolerances and functional clearances, these components are rotational misaligned (i.e. away from the nominal) by more than a specified, allowable rotation, the detent 106*d* and the ramp 112*p* come into contact (see FIG. 19). The contact of the alignment ramp 112*p* and the detent 106*d* combined with the angle of their sloped sides, acts to guide the clearance 106 and the blocking feature 112 back towards their nominal position depicted in FIG. 18. The corrected dispense position is shown in FIG. 20. In this position the blocking feature 112 is fully placed within the clearance 106 (see the regular edge 112*e* of the blocking feature 112 in FIG. 20) and is allowed to travel through the clearance 106 in order to initiate dose dispense.

The embodiments shown in FIGS. 21*a* to 26*b* are directed to control the maximum and/or the minimum dose that could be dialed by the device. If the user is allowed to dial higher than a maximum dose exceeding the maximum permitted dose within the track during dose dispense, the blocking feature 112 would run into the back of the track, impeding dispense and may jam the device. At the minimum dose dial stop the problem is reverse: the stop location required to stop dispense at zero units would block the dialing path of the opposing blocking feature. The following embodiments describe various dial stop designs which overcome this issue and allow fully configurable maximum doses for the device depicted in FIGS. 1 to 5. The designs may similarly also be provided with the device described with reference to FIGS. 6 to 9.

In the embodiment shown in FIGS. 21*a* and 21*b* the hands of the threads on limiter 100 and number sleeve 60 as well as gauge element 110 are reversed compared with the embodiment depicted in FIGS. 1 to 5. The effect of this, assuming all other components within the device remain the same, is that the gauge element 110 now travels in the opposite direction during dialing and dispense such that the maximum dose stop feature 104*a* now sits at the distal end of the device. Distal axial movement of the limiter 100 relative to the gauge element 110 now results in the blocking feature 112 moving away from the dose stop (rather than towards it, as in the embodiment shown in FIGS. 1 to 5) and as a result, the maximum dose dial stop feature 104*a* on the limiter 100 is located in the dialing path 102 of the blocking feature 112 without impeding the blocking feature 112 during dispense.

The minimum dose dial stop (e.g. the zero unit dial stop) is formed in this embodiment for example by using the interaction between the number sleeve 60 and the gauge element 110 rather than the limiter 100 and the gauge element 110. This is achieved by reacting a proximal end face 111*d* of the helical feature 111 of the gauge element 110 against the proximal end face 61*d* of the thread 61 of the number sleeve 60. The location of the faces 111*d* and 61*d* is shown in FIG. 22. The proximal end faces 111*d*, 61*d* run parallel to the axial direction I.

In the embodiment shown in FIGS. 23*a* to 24*b* the hands of the threads on limiter 100, gauge element 110 and number sleeve 60 are the same as in the embodiment shown in FIGS. 1 to 5. In this embodiment, the maximum dose stop feature 105*d* and the minimum dose stop feature 104*d* extend across two adjacent grooves 102 forming an axial edge or face and run transverse along two adjacent grooves 102 and one intermediate rib 103. In this embodiment it is assumed that only one maximum or minimum dialing feature is sufficient to withstand the prerequisite blocking load. Using only one feature removes the risk of a dial stop impeding the travel of a second blocking feature. FIGS. 23*a* and 23*b* show the blocking feature 112 in the maximum dose dial position, wherein in FIGS. 24*a* and 24*b* the blocking feature 112 is in the minimum dose dial position.

In the embodiment shown in FIGS. 25 and 26 unlike the previous embodiment avoids placing the maximum dose stop feature in the dialing or dispense groove 102 of the gauge element 110. Instead this embodiment uses a larger diameter stop that acts against a leading edge 113 of the gauge element 110 as shown in FIG. 25. Leading edge 113 of the gauge element 110 is designed to be longer in axial direction than a trailing edge (not shown) to ensure that the leading edge 113 engages with the stop feature 109 on the limiter 100 during dialing while the trailing edge misses this stop feature 109 during dispense. The stop feature 109 at the limiter 100 may be formed as a projection with a face running in axial direction to which the leading edge 113 of the gauge element 110 abuts when the maximum dose is dialed (see FIG. 25*b*). The leading edge 113 of the gauge element 110 is formed by a step-like structure formed at its proximal end. The leading edge 113 runs in axial direction. The maximum dose stop feature 109 is formed within the groove 102 of the limiter 100 at the proximal end of the groove 102.

As shown in FIGS. 26*a* and 26*b*, the minimum dose a user can dial in this embodiment is limited by the blocking feature 112 on the gauge element 110 reacting against the number sleeve 60. Unlike the limiter 100, the number sleeve 60 remains fixed axially relative to the gauge element 110 as the button 70 is pressed which means any stops formed on the number sleeve 60 would always be in the right position to provide dialing or dispense stops against the blocking feature 112 on the gauge element 110. The minimum dose stop 60*a* is formed on a step-like structure at the distal end of the number sleeve 60 providing an edge which runs axially. The blocking feature 112 abuts this minimum dose stop 60*a* when the minimum dose a user can dial is reached. By this embodiment, the travel of the opposite blocking feature (rib 103) at the limiter 100 is not impeded during dialing.

In another embodiment an additional component which is both axially and rotationally locked to the number sleeve may be provided to limit the maximum dialable dose. This component allows the limiter 100 to translate axially between it and the number sleeve.

REFERENCE NUMERALS

10, 10' housing
10*a* helical housing rib
11*a*, 11*b* window
11' window
20, 20' cartridge holder
30, 30' piston rod (plunger)
40 drive sleeve
50 nut
60, 60' dose selecting element (number sleeve)
60*a* minimum dose stop
61 thread
61*a* proximal face
61*b* distal face
61*d* proximal end face
62 spline
70 button (trigger)
71 groove
80 dose selector
90, 90' torsion spring
100, 100' limiter
101 spline
102, 102' groove
103 rib
103*a* serration
103*b* proximal face of rib 103
103*c* distal face of rib 103
103*d* detent
104 zero dose stop
105 maximum dose stop
106 clearance
106*a* ramp
106*d* positive detent
107 pin
108 pin
109 stop feature
110 gauge element
111 helical feature (thread segment)
111*a* proximal face
111*b* distal face
111*d* proximal face
112 blocking feature
112' track
112*a* distal face
112*b* proximal face
112*e* regular edge
112*g* lead-in ramp
112*p* alignment ramp
113 leading edge
120 clutch plate
130 clutch spring
I axis
D arrow showing distal direction
P arrow showing proximal direction

The invention claimed is:

1. A drug delivery device for selecting and dispensing a number of doses of a medicament, the drug delivery device comprising:
- a medicament reservoir attached to a housing;
- a drive mechanism comprising a plunger axially movable relative to the housing for dispensing doses of the medicament from the medicament reservoir;
- a dose selecting element releasably coupled to the drive mechanism and rotatable relative to the housing in a first direction for selecting a dose;
- a trigger axially movable relative to the housing for initiating dispensing of a dose selected by the dose selecting element; and
- a limiter configured to selectively permit and prevent axial movement of the trigger depending on an amount of the selected dose, wherein the limiter is
  - permanently rotationally constrained to the dose selecting element or
  - permanently axially guided within the housing,
- wherein the limiter is axially constrained to the trigger, wherein one of
  - the limiter or
  - a component part axially coupled to the housing comprises a track that is in engagement with a blocking feature of the other one of
  - the limiter and
  - the component part, and
- wherein the track comprises at least one narrow section limiting relative axial movement between the track and the blocking feature and at least one wide section permitting relative axial movement between the track and the blocking feature.

2. The drug delivery device according to claim 1, wherein the track extends helically or circumferentially about an outer surface of the limiter.

3. The drug delivery device according to claim 1, wherein the narrow section of the track defines a guidance for the blocking feature that is free of backlash.

4. The drug delivery device according to claim 1, wherein the track is a groove defined by at least one intermittent rib, wherein the narrow section of the track is defined by a portion of the groove in which the rib is present, and the wide section of the track is defined by a portion of the groove in which the rib is omitted.

5. The drug delivery device according to claim 4, wherein a face of the at least one intermittent rib directed opposite to the axial movement of the trigger is shallower than a face of the rib pointing in a direction of the axial movement, and a face of the blocking feature pointing in the direction of the axial movement is shallower than a face of the blocking feature directed opposite to the axial movement.

6. The drug delivery device according to claim 4, wherein a face of the at least one intermittent rib directed opposite to the axial movement of the trigger comprises at least one detent sized such that the blocking feature runs in clearance of the detent.

7. The drug delivery device according to claim 4, wherein the wide section of the track comprises a commit ramp.

8. The drug delivery device according to claim 1, wherein the track and the blocking feature are designed such that the blocking feature is prevented from passing over the narrow section of the track in an axial direction of movement of the trigger for initiating dispensing of a dose, and the blocking feature is permitted to pass over the narrow section of the track in a non-destructive manner in an opposite axial direction.

9. The drug delivery device according to claim 1, wherein the dose selecting element is a tubular number sleeve that is at least partially visible through an aperture or window of the housing and in threaded engagement with the housing or the component part.

10. The drug delivery device according to claim 9, wherein the limiter is in splined engagement with the dose selecting element such that the limiter is axially movable with respect to the dose selecting element.

11. The drug delivery device according to claim 9, wherein the component part is a gauge element that is rotationally constrained to the housing and axially movable relative to the housing, and wherein the dose selecting element is coupled to the gauge element by a thread.

12. The drug delivery device according to claim 11, wherein a proximal face of a rib forming a thread of the gauge element is shallower than a distal face of the rib, and a proximal face of a groove forming a thread of the dose selecting element is shallower than a distal face of the groove.

13. The drug delivery device according to claim 11, wherein the gauge element comprises an axial leading edge and an axial trailing edge at a proximal end of the gauge element.

14. The drug delivery device according to claim 13, wherein the axial leading edge is axially longer than the axial trailing edge.

15. The drug delivery device according to claim 11, wherein the dose selecting element is axially constrained to the housing.

16. The drug delivery device according to claim 11, wherein the gauge element comprises the blocking feature.

17. The drug delivery device according to claim 11, wherein the thread comprises at least one rotational hard stop configured to limit rotation of the dose selecting element relative to the gauge element.

18. The drug delivery device according to claim 9, wherein a proximal end of a portion comprising an outer thread of the tubular number sleeve comprises an axial edge.

19. The drug delivery device according to claim 1, wherein the dose selecting element is coupled to a power reservoir, and the power reservoir is coupled to the housing, such that rotation of the dose selecting element during dose selecting accumulates energy in the power reservoir.

20. The drug delivery device according to claim 1, comprising a clutch operable by the trigger and located between the dose selecting element and the drive mechanism, wherein the clutch rotationally couples the dose selecting element and the drive mechanism upon actuation of the trigger and permits relative rotation of the dose selecting element and the drive mechanism during dose selecting.

21. The drug delivery device according to claim 1, wherein the drive mechanism comprises a drive sleeve, and wherein the plunger is coupled to the housing and to the drive sleeve such that rotation of the drive sleeve causes axial movement of the plunger relative to the housing for dispensing doses of the medicament from the medicament reservoir.

22. The drug delivery device according to claim 21, wherein the plunger is in threaded engagement with the housing and in splined or threaded engagement with the drive sleeve.

23. The drug delivery device according to claim 1, wherein the track comprises at least one rotational hard stop configured to limit rotation of the blocking feature relative to the limiter.

24. The drug delivery device according to claim 1, wherein one or both of: i) the blocking feature, or ii) the at least one wide section of the track comprises an alignment feature.

25. The drug delivery device according to claim 1, wherein the dose selecting element constitutes the other component part and comprises the track, wherein the dose selecting element is in threaded engagement with the housing.

26. The drug delivery device according to claim 1, wherein the component part is axially coupled to the housing via a threaded engagement.

* * * * *